United States Patent
Fulga et al.

(10) Patent No.: US 12,018,256 B2
(45) Date of Patent: Jun. 25, 2024

(54) METHOD FOR MODIFYING GENES

(71) Applicant: OXFORD UNIVERSITY INNOVATION LIMITED, Oxford (GB)

(72) Inventors: Tudor A. Fulga, Oxford (GB); Yale S. Michaels, Oxford (GB); Thomas A. Milne, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 671 days.

(21) Appl. No.: 16/316,764

(22) PCT Filed: Jul. 13, 2017

(86) PCT No.: PCT/GB2017/052068
§ 371 (c)(1),
(2) Date: Jan. 10, 2019

(87) PCT Pub. No.: WO2018/011590
PCT Pub. Date: Jan. 18, 2018

(65) Prior Publication Data
US 2019/0292539 A1    Sep. 26, 2019

(30) Foreign Application Priority Data
Jul. 14, 2016  (GB) .................................. 1612214

(51) Int. Cl.
*C12N 15/11*  (2006.01)
*C12N 5/09*  (2010.01)
*C12N 15/63*  (2006.01)

(52) U.S. Cl.
CPC .......... *C12N 15/111* (2013.01); *C12N 5/0693* (2013.01); *C12N 15/63* (2013.01); *C12N 2310/141* (2013.01); *C12N 2310/51* (2013.01); *C12N 2330/51* (2013.01)

(58) Field of Classification Search
CPC .................. C12N 5/0693; C12N 2310/141
See application file for complete search history.

(56) References Cited

U.S. PATENT DOCUMENTS

| | | |
|---|---|---|
| 2007/0054872 A1 | 3/2007 | Reppen et al. |
| 2009/0023670 A1 | 1/2009 | Sebestyen |
| 2010/0041737 A1 | 2/2010 | Naldini et al. |
| 2013/0071430 A1 | 3/2013 | Nakamura et al. |

FOREIGN PATENT DOCUMENTS

| | | |
|---|---|---|
| WO | WO-2010/125471 A2 | 11/2010 |
| WO | WO-2013/007874 A1 | 1/2013 |
| WO | WO-2015/164786 A1 | 10/2015 |
| WO | WO-2017/062513 A1 | 4/2017 |

OTHER PUBLICATIONS

Ji et al (Seminars in Immunology 28 (2016) 45-53) (Year: 2016).*
Tan (Exp. Eye Res. 200 (2020) 108197, 11 pages (Year: 2020).*
Tan (Exp. Eye Res. 200 (2020) 108197, 4 pages of Appendices (Year: 2020).*
Feng et al (Biomed Rep. Oct. 2016; 5(4): 395-402) (Year: 2016).*
Menger et al (Cancer Res; 76(8): 2087-93, Apr. 2016) (Year: 2016).*
Xie et al., "Multi-input RNAi-based logic circuit for identification of specific cancer cells," Science. 333(6047):1307-11 (2011).
Bloom et al., "A quantitative framework for the forward design of synthetic miRNA circuits," Nat Methods. 11(11):1147-53 (including supplement) (2014) (11 pages).
Brown et al., "Endogenous microRNA can be broadly exploited to regulate transgene expression according to tissue, lineage and differentiation state," Nat Biotechnol. 25(12):1457-67 (2007).
Haley et al., "Kinetic analysis of the RNAi enzyme complex," Nat Struct Mol Biol. 11(7):599-606 (2004).
Wee et al., "Argonaute divides its RNA guide into domains with distinct functions and RNA-binding properties," Cell. 151(5):1055-67 (2012).
Schirle et al., "Structural basis for microRNA targeting," Science. 346(6209):608-13 (2014).
Broderick et al., "Argonaute protein identity and pairing geometry determine cooperativity in mammalian RNA silencing," RNA. 17(10):1858-69 (2011).
Bassett et al., "Understanding functional miRNA-target interactions in vivo by site-specific genome engineering," Nat Commun. 5:4640 (2014) (11 pages).
Cui et al., "Characterization of the microRNA pool and the factors affecting its regulatory potential," Integr Biol (Camb). 6(12):1141-52 (2014).
Geisler et al., "Application of mutated miR-206 target sites enables skeletal muscle-specific silencing of transgene expression of cardiotropic AAV9 vectors," Mol Ther. 21(5):924-33 (2013).
Gentner et al., "Exploiting microRNA regulation for genetic engineering," Tissue Antigens. 80(5):393-403 (2012).
Pucci et al., "A distinguishing gene signature shared by tumor-infiltrating Tie2-expressing monocytes, blood "resident" monocytes, and embryonic macrophages suggests common functions and developmental relationships," Blood. 114(4):901-14 (2009).
Schumann et al., "Generation of knock-in primary human T cells using Cas9 ribonucleoproteins," Proc Natl Acad Sci U S A. 112(33):10437-42 (2015).

(Continued)

*Primary Examiner* — Richard A Schnizer
(74) *Attorney, Agent, or Firm* — Clark & Elbing LLP

(57) ABSTRACT

The present invention relates to method of modulating the level of expression of an endogenous gene in a cell, the method comprising inserting a heterologous microRNA (miRNA) response element (MRE) into the 3'-untranslated region (3'-UTR) of the gene. The binding of endogenous miRNAs to the MRE results in or leads to a repression of the level of expression of the gene. The invention also relates to cells and transgenic animals whose endogenous genes comprise heterologous MRE in their 3'-UTRs.

Figure 1A:
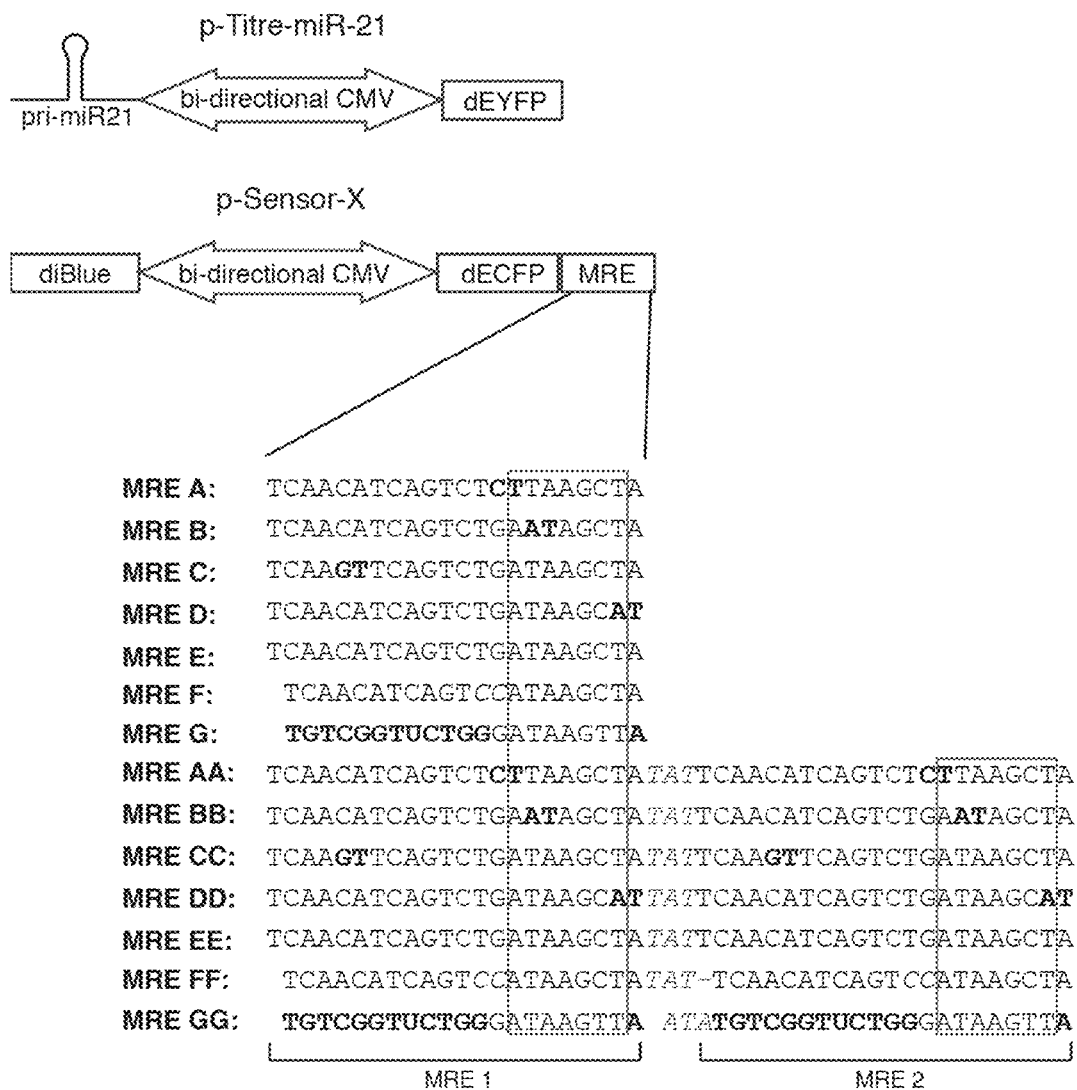

14 Claims, 20 Drawing Sheets
Specification includes a Sequence Listing.

(56) References Cited

OTHER PUBLICATIONS

Senís et al., "CRISPR/Cas9-mediated genome engineering: an adeno-associated viral (AAV) vector toolbox," Biotechnol J. 9(11):1402-12 (2014) (12 pages).
Su et al., "CRISPR-Cas9 mediated efficient PD-1 disruption on human primary T cells from cancer patients," Sci Rep. 6:20070 (2016) (13 pages).
Yang et al., "One-step generation of mice carrying reporter and conditional alleles by CRISPR/Cas-mediated genome engineering," Cell. 154(6):1370-9 (2013).
Michaels et al. "Precise tuning of gene expression levels in mammalian cells", Nature Communications. 10(1): 818 (Feb. 18, 2019) (12 pages).
Michaels et al. "Precise tuning of gene expression levels in mammalian cells", Nature Communications. 10(1): Supplementary Information (Feb. 18, 2019) (10 pages).

* cited by examiner

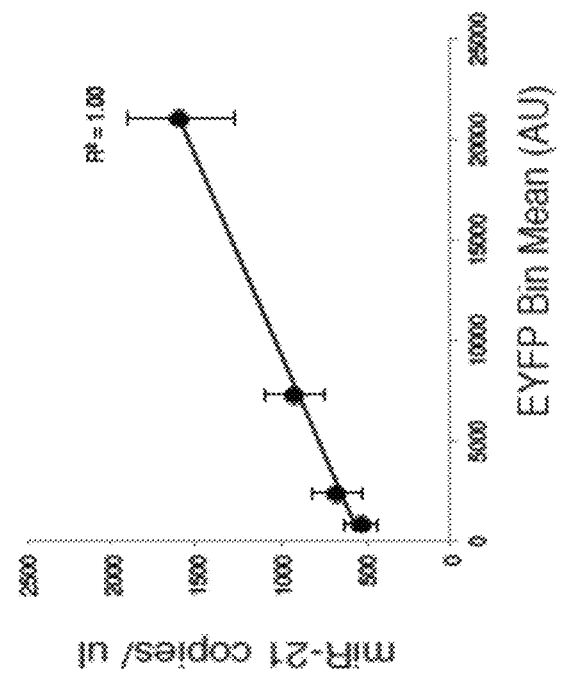
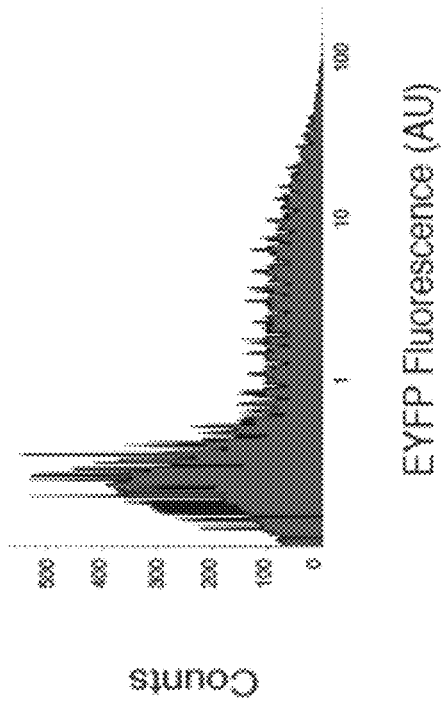
FIG. 2A
FIG. 2B
FIG. 2C

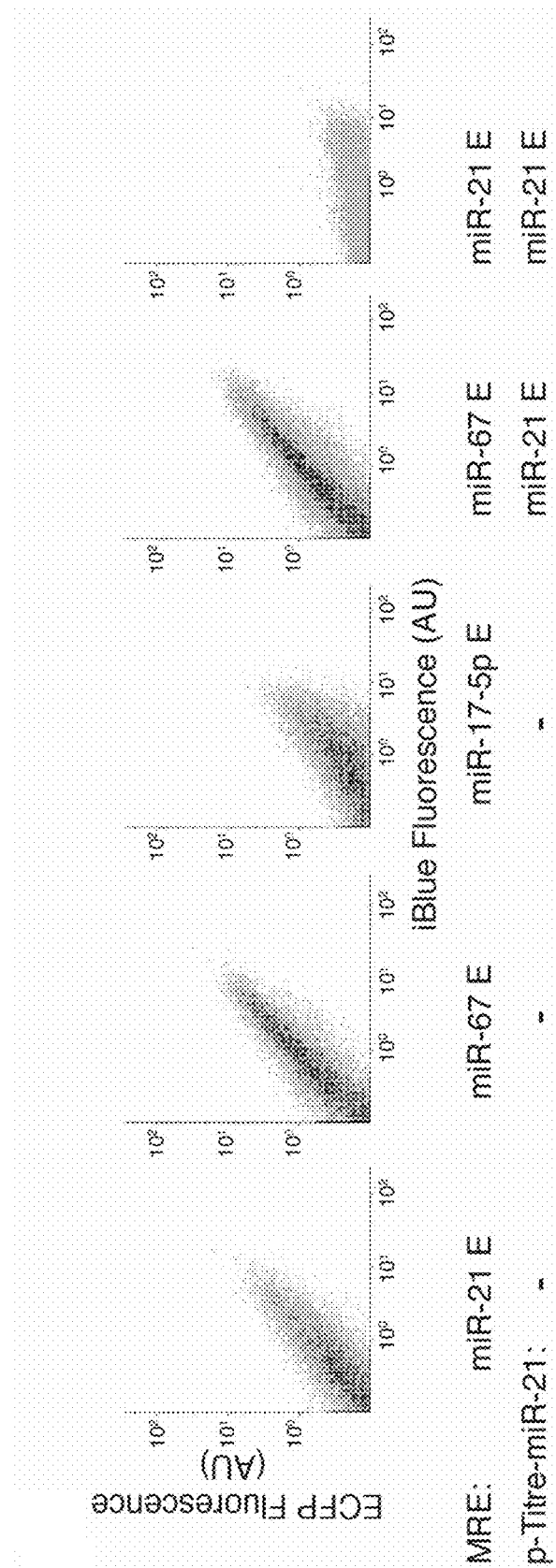

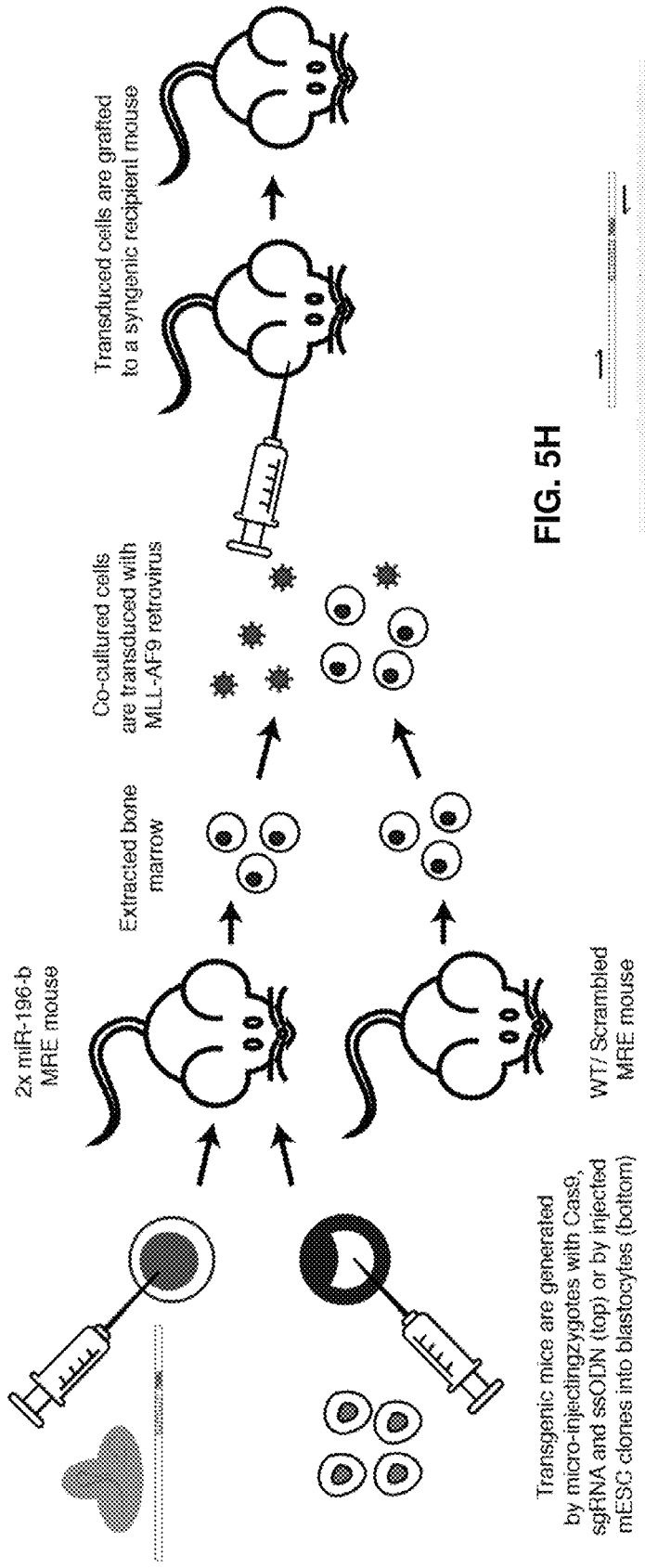
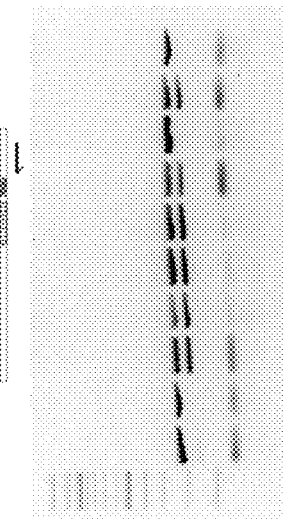
FIG. 5G
FIG. 5H

FIG. 6

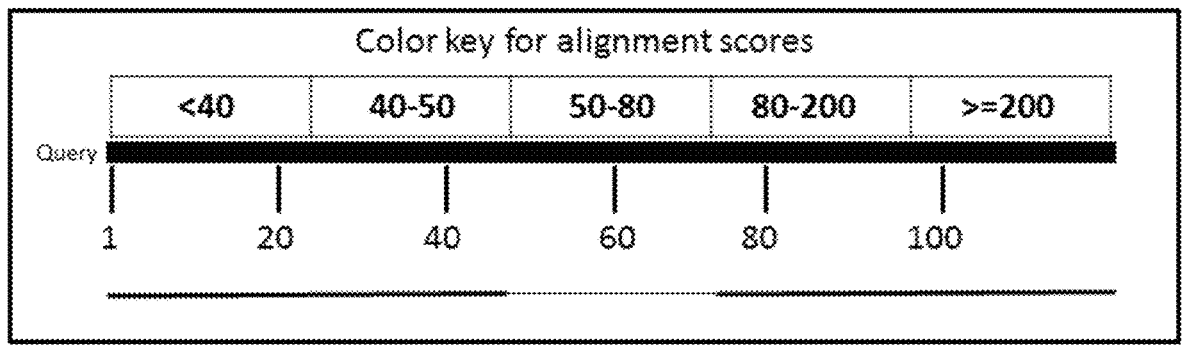

Distribution of 2 Blast Hits on the Query Sequence

FIG. 7

| Gene | microRNA | Position | Seed | dGduplex | dGopen | ddG |
|---|---|---|---|---|---|---|
| Seq1 | mmu-miR-21 | 59 | 8:0:0 | -35.5 | -5.48 | -30.01 |
| Seq1 | mmu-miR-127 | 67 | 8:1:0 | -23.94 | -9.62 | -14.31 |
| Seq1 | mmu-miR-762 | 40 | 8:1:1 | -23.2 | -10.35 | -12.84 |
| Seq1 | mmu-miR-541 | 68 | 8:1:1 | -20.41 | -9.85 | -10.55 |
| Seq1 | mmu-miR-675-5 | 104 | 8:1:1 | -22.3 | -12.04 | -10.25 |
| Seq1 | mmu-miR-770-3 | 43 | 8:1:1 | -20.7 | -10.57 | -10.12 |
| Seq1 | mmu-miR-154 | 59 | 8:1:0 | -13.3 | -5.48 | -7.81 |
| Seq1 | mmu-miR-33 | 23 | 8:1:1 | -18.7 | -10.95 | -7.74 |
| Seq1 | mmu-miR-10a | 15 | 8:1:1 | -13.8 | -6.16 | -7.63 |
| Seq1 | mmu-miR-380-5 | 27 | 8:1:1 | -18.3 | -11.21 | -7.08 |
| Seq1 | mmu-miR-151-3 | 52 | 8:0:1 | -17.5 | -10.74 | -6.75 |
| Seq1 | mmu-miR-743b | 74 | 8:0:1 | -20 | -13.26 | -6.73 |
| Seq1 | mmu-miR-770-3 | 35 | 8:1:1 | -20.8 | -14.11 | -6.68 |
| Seq1 | mmu-miR-199a | 19 | 8:1:1 | -17.9 | -11.21 | -6.68 |
| Seq1 | mmu-miR-199b | 19 | 8:1:1 | -17.9 | -11.21 | -6.68 |
| Seq1 | mmu-miR-361 | 55 | 8:1:0 | -14.44 | -8.15 | -6.28 |
| Seq1 | mmu-miR-345-3 | 24 | 8:1:1 | -18.1 | -11.96 | -6.13 |
| Seq1 | mmu-miR-412 | 41 | 8:1:0 | -15.4 | -10.36 | -5.03 |
| Seq1 | mmu-miR-10b | 15 | 8:1:1 | -11.1 | -6.16 | -4.93 |
| Seq1 | mmu-miR-450b | 37 | 8:1:1 | -18.57 | -14.27 | -4.29 |
| Seq1 | mmu-miR-666-3 | 20 | 8:1:1 | -15 | -10.87 | -4.12 |
| Seq1 | mmu-miR-423-3 | 74 | 8:1:1 | -16.9 | -13.26 | -3.63 |
| Seq1 | mmu-miR-184 | 70 | 8:1:1 | -16.47 | -12.86 | -3.6 |
| Seq1 | mmu-miR-687 | 65 | 8:1:1 | -13.6 | -10.04 | -3.55 |

SEQUENCE LISTING

```
<160> NUMBER OF SEQ ID NOS: 30

<210> SEQ ID NO 1
<211> LENGTH: 23
<212> TYPE: RNA
<213> ORGANISM: Artificial Sequence
<220> FEATURE:
```

```
<223> OTHER INFORMATION: miR-17 microRNA sequence

<400> SEQUENCE: 1
caaagugcuu acagugcagg uag                                              23

<210> SEQ ID NO 2
<211> LENGTH: 23
<212> TYPE: DNA
<213> ORGANISM: Artificial Sequence
<220> FEATURE:
<223> OTHER INFORMATION: miR-17 Perfect MRE DNA sequence

<400> SEQUENCE: 2
ctacctgcac tgtaagcact ttg                                              23

<210> SEQ ID NO 3
<211> LENGTH: 23
<212> TYPE: RNA
<213> ORGANISM: Artificial Sequence
<220> FEATURE:
<223> OTHER INFORMATION: miR-19 microRNA sequence

<400> SEQUENCE: 3
ugugcaaauc uaugcaaaac uga                                              23

<210> SEQ ID NO 4
<211> LENGTH: 23
<212> TYPE: DNA
<213> ORGANISM: Artificial Sequence
<220> FEATURE:
<223> OTHER INFORMATION: miR-19 Perfect MRE DNA sequence

<400> SEQUENCE: 4
tcagttttgc atagatttgc aca                                              23

<210> SEQ ID NO 5
<211> LENGTH: 22
<212> TYPE: RNA
<213> ORGANISM: Artificial Sequence
<220> FEATURE:
<223> OTHER INFORMATION: miR-21 microRNA sequence

<400> SEQUENCE: 5
uagcuuauca gacugauguu ga                                               22

<210> SEQ ID NO 6
<211> LENGTH: 22
<212> TYPE: DNA
<213> ORGANISM: Artificial Sequence
<220> FEATURE:
<223> OTHER INFORMATION: miR-21 Perfect MRE DNA sequence

<400> SEQUENCE: 6
tcaacatcag tctgataagc ta                                               22

<210> SEQ ID NO 7
<211> LENGTH: 23
<212> TYPE: RNA
<213> ORGANISM: Artificial Sequence
<220> FEATURE:
<223> OTHER INFORMATION: miR-155 microRNA sequence

<400> SEQUENCE: 7
uuaaugcuaa ucgugauagg ggu                                              23
```

```
<210> SEQ ID NO 8
<211> LENGTH: 23
<212> TYPE: DNA
<213> ORGANISM: Artificial Sequence
<220> FEATURE:
<223> OTHER INFORMATION: miR-155 Perfect MRE DNA sequence

<400> SEQUENCE: 8
acccctatca cgattagcat taa                                          23

<210> SEQ ID NO 9
<211> LENGTH: 22
<212> TYPE: RNA
<213> ORGANISM: Artificial Sequence
<220> FEATURE:
<223> OTHER INFORMATION: miR-196b microRNA sequence

<400> SEQUENCE: 9
uagguaguuu ccuguuguug gg                                           22

<210> SEQ ID NO 10
<211> LENGTH: 22
<212> TYPE: DNA
<213> ORGANISM: Artificial Sequence
<220> FEATURE:
<223> OTHER INFORMATION: miR-196b Perfect MRE DNA sequence

<400> SEQUENCE: 10
cccaacaaca ggaaactacc ta                                           22

<210> SEQ ID NO 11
<211> LENGTH: 22
<212> TYPE: RNA
<213> ORGANISM: Artificial Sequence
<220> FEATURE:
<223> OTHER INFORMATION: miR-92 microRNA sequence

<400> SEQUENCE: 11
uauugcacuu gucccggccu gu                                           22

<210> SEQ ID NO 12
<211> LENGTH: 22
<212> TYPE: DNA
<213> ORGANISM: Artificial Sequence
<220> FEATURE:
<223> OTHER INFORMATION: miR-92 Perfect MRE DNA sequence

<400> SEQUENCE: 12
acaggccggg acaagtgcaa ta                                           22

<210> SEQ ID NO 13
<211> LENGTH: 22
<212> TYPE: RNA
<213> ORGANISM: Artificial Sequence
<220> FEATURE:
<223> OTHER INFORMATION: miR-126 microRNA sequence

<400> SEQUENCE: 13
ucguaccgug aguaauaaug cg                                           22

<210> SEQ ID NO 14
<211> LENGTH: 22
<212> TYPE: DNA
<213> ORGANISM: Artificial Sequence
<220> FEATURE:
<223> OTHER INFORMATION: miR-126 Perfect MRE DNA sequence
```

```
<400> SEQUENCE: 14
cgcattatta ctcacggtac ga                                              22

<210> SEQ ID NO 15
<211> LENGTH: 22
<212> TYPE: RNA
<213> ORGANISM: Artificial Sequence
<220> FEATURE:
<223> OTHER INFORMATION: miR-148a microRNA sequence

<400> SEQUENCE: 15
ucagugcacu acagaacuuu gu                                              22

<210> SEQ ID NO 16
<211> LENGTH: 22
<212> TYPE: DNA
<213> ORGANISM: Artificial Sequence
<220> FEATURE:
<223> OTHER INFORMATION: miR-148a Perfect MRE DNA sequence

<400> SEQUENCE: 16
acaaagttct gtagtgcact ga                                              22

<210> SEQ ID NO 17
<211> LENGTH: 22
<212> TYPE: DNA
<213> ORGANISM: Artificial Sequence
<220> FEATURE:
<223> OTHER INFORMATION: MRE A

<400> SEQUENCE: 17
tcaacatcag tctcttaagc ta                                              22

<210> SEQ ID NO 18
<211> LENGTH: 22
<212> TYPE: DNA
<213> ORGANISM: Artificial Sequence
<220> FEATURE:
<223> OTHER INFORMATION: MRE B

<400> SEQUENCE: 18
tcaacatcag tctgaatagc ta                                              22

<210> SEQ ID NO 19
<211> LENGTH: 22
<212> TYPE: DNA
<213> ORGANISM: Artificial Sequence
<220> FEATURE:
<223> OTHER INFORMATION: MRE C

<400> SEQUENCE: 19
tcaagttcag tctgataagc ta                                              22

<210> SEQ ID NO 20
<211> LENGTH: 22
<212> TYPE: DNA
<213> ORGANISM: Artificial Sequence
<220> FEATURE:
<223> OTHER INFORMATION: MRE D

<400> SEQUENCE: 20
tcaacatcag tctgataagc at                                              22

<210> SEQ ID NO 21
<211> LENGTH: 22
```

```
<212> TYPE: DNA
<213> ORGANISM: Artificial Sequence
<220> FEATURE:
<223> OTHER INFORMATION: MRE E

<400> SEQUENCE: 21
tcaacatcag tctgataagc ta                                           22

<210> SEQ ID NO 22
<211> LENGTH: 21
<212> TYPE: DNA
<213> ORGANISM: Artificial Sequence
<220> FEATURE:
<223> OTHER INFORMATION: MRE F

<400> SEQUENCE: 22
tcaacatcag tccataagct a                                            21

<210> SEQ ID NO 23
<211> LENGTH: 21
<212> TYPE: DNA
<213> ORGANISM: Artificial Sequence
<220> FEATURE:
<223> OTHER INFORMATION: MRE G

<400> SEQUENCE: 23
tgtcggtuct gggataagtt a                                            21

<210> SEQ ID NO 24
<211> LENGTH: 47
<212> TYPE: DNA
<213> ORGANISM: Artificial Sequence
<220> FEATURE:
<223> OTHER INFORMATION: MRE AA

<400> SEQUENCE: 24
tcaacatcag tctcttaagc tatattcaac atcagtctct taagcta                47

<210> SEQ ID NO 25
<211> LENGTH: 47
<212> TYPE: DNA
<213> ORGANISM: Artificial Sequence
<220> FEATURE:
<223> OTHER INFORMATION: MRE BB

<400> SEQUENCE: 25
tcaacatcag tctgaatagc tatattcaac atcagtctga atagcta                47

<210> SEQ ID NO 26
<211> LENGTH: 47
<212> TYPE: DNA
<213> ORGANISM: Artificial Sequence
<220> FEATURE:
<223> OTHER INFORMATION: MRE CC

<400> SEQUENCE: 26
tcaagttcag tctgataagc tatattcaag ttcagtctga taagcta                47

<210> SEQ ID NO 27
<211> LENGTH: 47
<212> TYPE: DNA
<213> ORGANISM: Artificial Sequence
<220> FEATURE:
<223> OTHER INFORMATION: MRE DD

<400> SEQUENCE: 27
```

```
tcaacatcag tctgataagc attattcaac atcagtctga taagcat        47

<210> SEQ ID NO 28
<211> LENGTH: 47
<212> TYPE: DNA
<213> ORGANISM: Artificial Sequence
<220> FEATURE:
<223> OTHER INFORMATION: MRE EE

<400> SEQUENCE: 28
tcaacatcag tctgataagc tatattcaac atcagtctga taagcta        47

<210> SEQ ID NO 29
<211> LENGTH: 45
<212> TYPE: DNA
<213> ORGANISM: Artificial Sequence
<220> FEATURE:
<223> OTHER INFORMATION: MRE FF

<400> SEQUENCE: 29
tcaacatcag tccataagct atattcaaca tcagtccata agcta          45

<210> SEQ ID NO 30
<211> LENGTH: 45
<212> TYPE: DNA
<213> ORGANISM: Artificial Sequence
<220> FEATURE:
<223> OTHER INFORMATION: MRE GG

<400> SEQUENCE: 30
tgtcggtuct gggataagtt aatatgtcgg tuctgggata agtta          45
```

METHOD FOR MODIFYING GENES

The present invention relates to method of modulating the level of expression of an endogenous gene in a cell, the method comprising inserting a heterologous microRNA (miRNA) response element (MRE) into the 3'-untranslated region (3'-UTR) of the gene. The binding of endogenous miRNAs to the MRE results in or leads to a repression of the level of expression of the gene. The invention also relates to cells and transgenic animals whose endogenous genes comprise heterologous MRE in their 3'-UTRs.

Eukaryotic gene expression is a robust and finely-tuned process. The combined action of chromatin modifiers and readers (1), transcription factors and their interaction partners (2), and microRNAs and other post-transcriptional regulatory elements are critical to cellular function. Spatial-temporal control of gene regulation allows complex organisms, comprised of phenotypically-diverse tissues, to arise from a shared genome. Consequently, perturbations in gene expression programs can result in developmental defects and disease (1). Tools for precisely manipulating gene expression are thus highly sought-after by researchers and clinicians alike.

One strategy to study the role of a particular gene product in development and disease is to exogenously introduce (knock-in) or remove (knock-out) the gene in a context of interest. Knock-in/knock-out organisms have proven to be invaluable research tools across biological disciplines (3). However, a major limitation of these approaches is their inherent all-or-nothing nature. Knock-in and knockout strategies fail to recapitulate subtle changes in gene expression levels that are often associated with development, differentiation and disease (1).

Exogenous delivery of small interfering RNAs (siRNA) and related technologies can be employed to post-transcriptionally silence a gene of interest. However, the maximum level of down-regulation that can be achieved by siRNAs varies widely from one gene target to another and cannot easily be controlled (4). Furthermore, the utility of siRNAs is impaired by their lack of specificity and the difficulty of targeted nucleic acid delivery in vivo (5, 6).

There is a need therefore to develop a tool for fine-tuning endogenous gene expression in a manner that overcomes the aforementioned limitations.

miRNAs are short regulatory RNAs that function in plants and animals by guiding the miRNA-induced silencing complex (miRISC) to RNA targets bearing a complementary "seed" sequence (9).

The binding of a miRNA to the seed sequence results in attenuation of gene expression (protein production for coding genes); possible mechanisms include translational inhibition and target mRNA destabilization and decay.

It has previously been shown that, by inserting miRNA response elements (MREs) into the 3'-untranslated region (3'-UTR) of a transgene of interest, it may be possible to post-transcriptionally down-regulate expression in a predictable manner (7, 8).

In particular, US2010/0041737 A1 discloses the use of vectors comprising a transgene and a miRNA target sequence. The miRNA target sequences are recognised by endogenous miRNAs, thus enabling cell-type specific expression of the associated transgenes. Furthermore, US2010/0041737 A1 discloses that different miRNAs are expressed endogenously at different levels. Therefore, different miRNA/target sequence combinations can be selected to provide a range of different expression levels of the transgene. However, this publication relates only to the use of transgenes, i.e. exogenously-supplied genes; it does not relate to the manipulation of endogenous genes.

There remains a need, therefore, for a method of modulating the expression levels of endogenous genes within cells.

The inventors have now found that it is possible to insert a heterologous MRE into the 3'-UTR of an endogenous gene and to make use of the cell's own endogenous miRNAs to control the expression/repression of the endogenous gene. Importantly, it has been found that the level of sequence complementarity between the miRNA and the heterologous MRE can be used to vary the binding affinity between the miRNA and the MRE; this influences the level of repression of the associated gene.

By designing a panel of MREs with various nucleotide sequence identities to the parent MRE, and consequently differential affinity for an endogenous effector miRNA, it has been possible to create a miRNA-driven "rheostat" which is capable of fine-tuning gene expression levels in a user-defined manner.

The current invention therefore enables precise and specific modulation of endogenous gene-transcript levels both in cell culture and in vivo.

In a first embodiment, the invention provides a method of modulating the level of expression of a gene in a cell, wherein the gene is expressed or is capable of being expressed in the cell, wherein the cell is one which expresses a miRNA or is capable of expressing the miRNA, the method comprising the step:

(i) inserting a heterologous MRE into the 3'-UTR of the gene, wherein the heterologous MRE is one which is capable of being bound by the miRNA with a first affinity, and wherein the binding of the miRNA to the MRE results in or leads to a reduction of the level of expression of the gene.

Preferably, the nucleotide sequence of the MRE is selected such that the binding of the miRNA to the MRE results in or leads to a desired reduction of the level of expression of the gene. Preferably, the level of complementarity between the nucleotide sequence of the MRE and the nucleotide sequence of the miRNA is selected such that the binding of the miRNA to the MRE results in or leads to a desired reduction of the level of expression of the gene.

The invention also provides a method for modifying an endogenous gene, the method comprising the step of (i) inserting a heterologous MRE into the 3'-UTR of the gene.

The invention also provides an isolated endogenous gene which has been modified by a method of the invention.

In a further embodiment, the invention provides a cell, wherein one or more of the cell's endogenous genes comprise a heterologous MRE in the gene's 3'-UTR; and a cell, wherein one or more of the cell's endogenous genes has been modified by the insertion of a heterologous MRE in the gene's 3'-UTR.

In a further embodiment, the invention provides a transgenic non-human animal, wherein one or more of the animal's endogenous genes comprise a heterologous MRE in the gene's 3'-UTR; and a transgenic non-human animal, wherein one or more of the animal's endogenous genes has been modified by the insertion of a heterologous MRE in the gene's 3'-UTR.

In a further embodiment, the invention provides a plurality of nucleic acid molecules, each nucleic acid molecule independently comprising:

(a) a gene comprising a different MRE, wherein the nucleotide sequences of the genes are the same apart from the nucleotide sequences of the MREs, wherein the nucleotide sequences of the MREs have all independently been derived from the nucleotide sequence of a common MRE to produce modified MREs, and wherein the common MRE is capable of being bound by a miRNA with a first affinity, and wherein the modified MREs are capable of being bound by the miRNA with a plurality of different affinities. Preferably, the common MRE is a native MRE.

The invention also provides a plurality of vectors each comprising a nucleic acid molecule as defined above.

As used herein, the term "gene" encompasses any sequence of nucleotides that encodes a mRNA, non-coding RNA, short hairpin RNA or protein-coding RNA.

The gene may be any gene whose expression it is desired to control. The gene may, for example, be a prokaryotic or eukaryotic gene, preferably a eukaryotic gene, more preferably an animal gene. Examples of animal genes include mammalian genes, preferably mouse genes or human genes. The gene may be a derivative or variant of a native/wild-type gene. In some embodiments, the gene is one which codes for a transcription factor, chromatin protein, oncogene, receptor, kinase, proto-oncogene or DNA binding protein.

In some preferred embodiments, the gene is selected from the group consisting of TYK2, CD8, CD3, CD28, IL2, IL10, BNIP3, CCR5, CD4, BRCA1, BRCA2, LEP, LIF, RHO, RAC, CXCR4, PDL1, PDL2, CD80, CD40, P53, mTOR, Myc, B-Catenin, Caspase 9, Oct-4, Sox2, Nanog, HIF1A, HBE1, HBG2, HBG1, HBD, HBB, HRAS, KRAS, c-Sis, EGFR, PDGFR-A, PDGFR-B, PDGFR-C, PDGFR-D, VEGFR-1, VEGFR-2, HER2, RAF, RET, CDK1, CDK2, CDK4, CDK6, ABL, PARP-1, BRAF, ALK, PTEN, PLK1, Aurora-B, HSF1, PDK, MHCI, MHCII and PGE2. Preferably, the gene is selected from the group consisting of MYB, PD-1, LAG-3, TIM-3, BTLA, CTLA-4, HBA1, HBA2 and BCL-2.

As used herein, the term "endogenous gene" refers to a gene when present in its natural state, i.e. within a cell. The term "endogenous" may be contrasted with the term "transgene" which refers to a heterologous gene (which does not occur naturally within the cell) which has been (artificially) introduced into the cell. The endogenous gene may be present within the genome of the cell or within the mitochondrial genome.

The 3'-untranslated region (3'-UTR) is the section of mRNA that immediately follows the translation termination codon. The 3'-UTR often contains regulatory regions that post-transcriptionally influence gene expression.

Regulatory regions within the 3'-UTR can influence polyadenylation, translation efficiency, localization and stability of the mRNA. The 3'-UTR contains binding sites for regulatory proteins as well as microRNAs (miRNAs). The 3'-UTR also has silencer regions which bind to repressor proteins and will inhibit the expression of the mRNA. Many 3'-UTRs also contain AU-rich elements (AREs). Furthermore, the 3'-UTR contains the sequence AAUAAA that directs addition of the poly(A) tail to the end of the mRNA transcript.

The 3'-UTR can also contain sequences that attract proteins to associate the mRNA with the cytoskeleton, transport it to or from the cell nucleus, or perform other types of localization. In addition to sequences within the 3'-UTR, the physical characteristics of the region, including its length and secondary structure, contribute to translation regulation.

The length of the 3'-UTR in the mammalian genome has considerable variation: it can range from 60 nucleotides to about 4000. On average, the length for the 3'-UTR in humans is approximately 800 nucleotides, while the average length of 5'-UTRs (in all organisms) is only about 200 nucleotides. The length of the 3'-UTR is significant since longer 3'-UTRs are associated with lower levels of gene expression.

microRNAs (miRNAs) are small non-coding RNA molecules (containing about 22 nucleotides) found in plants, animals and some viruses, that function in RNA-silencing and post-transcriptional regulation of gene expression. A miRNA is complementary to a part of one or more messenger RNAs (mRNAs).

Animal miRNAs are usually complementary to a site in the 3'-untranscribed region (3'-UTR), i.e. the miRNA Response Element or MRE. Perfect base pairing with the target RNA promotes cleavage of the RNA. Near-perfect base-pairing with the target RNA promotes degradation of the RNA by other pathways.

MREs are usually 6-25 nucleotides in length. Preferably, the MREs used herein are 18-24, more preferably 20-22 nucleotides in length.

The binding of a miRNA to its cognate MRE results in or leads to repression of the associated gene or genes.

In canonical miRNA regulation, the MRE comprises a "seed region" of 6-7 nucleotides. Bona fide miRNA targets often contain complementarity to nucleotides 2 to 8 from the 5' end of their cognate microRNA; this region is known as the seed. Complementarity between the target transcript and the 3'-end of the cognate microRNA may help compensate for weaker pairing in the 5'-seed region.

Preferably, the miRNA is one which is differentially-expressed in a human disease.

Preferred examples of heterologous MREs (and reference MREs) include those which are bound by (e.g. those whose nucleotide sequences are complementary to or partially complementary to) the following miRNAs:

hsa-let-7a, hsa-let-7a-1, hsa-let-7a-2, hsa-let-7a-3, hsa-let-7b, hsa-let-7b*, hsa-let-7c, hsa-let-7d, hsa-let-7d*, hsa-let-7e, hsa-let-7e*, hsa-let-7f, hsa-let-7f-1, hsa-let-7f-2, hsa-let-7g, hsa-let-7i, hsa-miR-1, hsa-miR-1-2, hsa-miR-100, hsa-miR-100-1, hsa-miR-100-2, hsa-miR-101, hsa-miR-101-1, hsa-miR-101a, hsa-miR-101b-2 hsa-miR-102, hsa-miR-103, hsa-miR-103-1, hsa-miR-103-2, hsa-miR-104, hsa-miR-105, hsa-miR-106a, hsa-miR-106a-1, hsa-miR-106b, hsa-miR-106b-1, hsa-miR-107, hsa-miR-10a, hsa-miR-10b, hsa-miR-122, hsa-miR-122a, hsa-miR-1228*, hsa-miR-123, hsa-miR-124a, hsa-miR-124a-1, hsa-miR-124a-2, hsa-miR-124a-3, hsa-miR-125a, hsa-miR-125a-5p, hsa-miR-125b, hsa-miR-125b-1, hsa-miR-125b-2, hsa-miR-126, hsa-miR-126-5p, hsa-miR-126*, hsa-miR-127, hsa-miR-128a, hsa-miR-128b, hsa-miR-129, hsa-miR-129-1, hsa-miR-129-2, hsa-miR-130, hsa-miR-130a, hsa-miR-130a-1, hsa-miR-130b, hsa-miR-130b-1, hsa-miR-132, hsa-miR-133a, hsa-miR-133b, hsa-miR-134, hsa-miR-135a, hsa-miR-135b, hsa-miR-136, hsa-miR-137, hsa-miR-138, hsa-miR-138-1, hsa-miR-138-2, hsa-miR-139, hsa-miR-139-5p, hsa-miR-140, hsa-miR-140-3p, hsa-miR-140*, hsa-miR-141, hsa-miR-142-3p, hsa-miR-142-5p, hsa-miR-143, hsa-miR-144, hsa-miR-144*, hsa-miR-145, hsa-miR-146a, hsa-miR-146a*, hsa-miR-146b, hsa-miR-147, hsa-miR-148a, hsa-miR-148b, hsa-miR-149, hsa-miR-15, hsa-miR-150, hsa-miR-151, hsa-miR-151-5p, hsa-miR-151*, hsa-miR-152, hsa-miR-153, hsa-miR-154, hsa-miR-154*, hsa-miR-155, hsa-miR-15a, hsa-miR-15a-2, hsa-miR-15b, hsa-miR-16, hsa-miR-16-1, hsa-miR-16-2, hsa-miR-16a, hsa-miR-164, hsa-miR-170, hsa-miR-172a-2, hsa-miR-17, hsa-miR-17-3p, hsa-miR-17-5p, hsa-miR-17-92, hsa-miR-18, hsa-miR-18a, hsa-miR-18b, hsa-miR-18a*, hsa-miR-181a, hsa-miR-181a-1, hsa-miR-181a-2, hsa-miR-181a*, hsa-miR-181a-1*, hsa-miR-181b, hsa-miR-181b-1, hsa-miR-181b-2, hsamiR-181c, hsa-miR-181d, hsa-miR-182, hsa-miR-182*, hsa-miR-183, hsa-miR-184, hsa-miR-185, hsa-miR-186, hsa-miR-187, hsa-miR-188, hsa-miR-189, hsa-miR-190, hsa-miR-191, hsa-miR-192, hsa-miR-192-1, hsa-miR-192-2, hsa-miR-192-3, hsa-miR-193a, hsa-miR-193b, hsa-miR-194, hsa-miR-195, hsa-miR-195*, hsa-miR-196a, hsa-miR-196a-2, hsa-miR-196b, hsa-miR-197, hsa-miR-198, hsa-miR-199a, hsa-miR-199a-1, hsa-miR-199a-1-5p, hsa-miR-199a-2, hsa-miR-199a-2-5p, hsa-miR-199a-3p, hsa-miR-199b, hsa-miR-199b-5p, hsa-miR-19a, hsa-miR-19b, hsa-miR-19b-1, hsa-miR-19b-2, hsa-miR-200a, hsa-miR-200b, hsa-miR-200c, hsa-miR-202, hsa-miR-203, hsa-miR-204, hsa-miR-205, hsa-miR-206, hsa-miR-207, hsa-miR-208, hsa-miR-208a, hsa-miR-20a, hsa-miR-20b, hsa-miR-21, hsa-miR-22, hsa-miR-210, hsa-miR-211, hsa-miR-212, hsa-miR-213, hsa-miR-214, hsa-miR-215, hsa-miR-216, hsa-miR-217, hsa-miR-218, hsa-miR-218-2, hsa-miR-219, hsa-miR-219-1, hsa-miR-22, hsa-miR-220, hsa-miR-221, hsa-miR-222, hsa-miR-223, hsa-miR-224, hsa-miR-23a, hsa-miR-23b, hsa-miR-24, hsa-miR-24-1, hsa-miR-24-2, hsa-miR-25, hsa-miR-26a, hsa-miR-26a-1, hsa-miR-26a-2, hsa-miR-26b, hsa-miR-27a, hsa-miR-27b, hsa-miR-28, hsa-miR-296, hsa-miR-298, hsa-miR-299-3p, hsa-miR-299-5p, hsa-miR-29a, hsa-miR-29a-2, hsa-miR-29b, hsa-miR-29b-1, hsa-miR-29b-2, hsa-miR-29c, hsa-miR-301, hsa-miR-302, hsa-miR-302a, hsa-miR-302b, hsa-miR-302b*, hsa-miR-302c, hsa-miR-302c*, hsa-miR-302d, hsa-miR-30a, hsa-miR-30a-3p, hsa-miR-30a-5p, hsa-miR-30b, hsa-miR-30b*, hsa-miR-30c, hsa-miR-30c-1, hsa-miR-30d, hsa-miR-30e, hsa-miR-30e*, hsa-miR-30e-5p, hsa-miR-31, hsa-miR-31a, hsa-miR-32, hsa-miR-32*, hsa-miR-320, hsa-miR-320-2, hsa-miR-320a, hsa-miR-322, hsa-miR-323, hsa-miR-324-3p, hsa-miR-324-5p, hsa-miR-325, hsa-miR-326, hsa-miR-328, hsa-miR-328-1, hsa-miR-33, hsa-miR-330, hsa-miR-331, hsa-miR-335, hsa-miR-337, hsa-miR-337-3p, hsa-miR-338, hsa-miR-338-5p, hsa-miR-339, hsa-miR-339-5p, hsa-miR-34a*, hsa-miR-340, hsa-miR-340*, hsa-miR-341, hsa-miR-342, hsa-miR-342-3p, hsa-miR-345, hsa-miR-346, hsa-miR-347, hsa-miR-34a, hsa-miR-34b, hsa-miR-34c, hsa-miR-351, hsa-miR-352, hsa-miR-361, hsa-miR-362, hsa-miR-363, hsa-miR-355, hsa-miR-365, hsa-miR-367, hsa-miR-368, hsa-miR-369-5p, hsa-miR-370, hsa-miR-371, hsa-miR-372, hsa-miR-373, hsa-miR-373*, hsa-miR-374, hsa-miR-375, hsa-miR-376a, hsa-miR-376b, hsa-miR-377, hsa-miR-378, hsa-miR-378*, hsa-miR-379, hsa-miR-381, hsa-miR-382, hsa-miR-383, hsa-miR-409-3p, hsa-miR-419, hsa-miR-422a, hsa-miR-422b, hsa-miR-423, hsa-miR-424, hsa-miR-429, hsa-miR-431, hsa-miR-432, hsa-miR-432*, hsa-miR-433, hsa-miR-449a, hsa-miR-451, hsa-miR-452, hsa-miR-451, hsa-miR-452, hsa-miR-452*, hsa-miR-483, hsa-miR-483-3p, hsa-miR-484, hsa-miR-485-5p, hsa-miR-485-3p, hsa-miR-486, hsa-miR-487b, hsa-miR-489, hsa-miR-491, hsa-miR-491-5p, hsa-miR-492, hsa-miR-493-3p, hsa-miR-493-5p, hsa-miR-494, hsa-miR-495, hsa-miR-497, hsa-miR-498, hsa-miR-499, hsa-miR-5, hsa-miR-500, hsa-miR-501, hsa-miR-503, hsa-miR-508, hsa-miR-509, hsa-miR-510, hsa-miR-511, hsa-miR-512-5p, hsa-miR-513, hsa-miR-513-1, hsa-miR-513-2, hsa-miR-515-3p, hsa-miR-516-5p, hsa-miR-516-3p, hsa-miR-518a-2*, hsa-miR-518b, hsa-miR-518c*, hsa-miR-519a, hsa-miR-519d, hsa-miR-520a, hsa-miR-520c, hsa-miR-521, hsa-miR-524*, hsa-miR-525*, hsa-miR-532-5p, hsa-miR-539, hsa-miR-542-3p, hsa-miR-542-5p, hsa-miR-550, hsa-miR-551a, hsa-miR-561, hsa-miR-563, hsa-miR-565, hsa-miR-572, hsa-miR-582, hsa-miR-584, hsa-miR-594, hsa-miR-595, hsa-miR-598, hsa-miR-599, hsa-miR-600, hsa-miR-601, hsa-miR-602, hsa-miR-605, hsa-miR-608, hsa-miR-611, hsa-miR-612, hsa-miR-614, hsa-miR-615, hsa-miR-615-3p, hsa-miR-622, hsa-miR-627, hsa-miR-628, hsa-miR-635, hsa-miR-637, hsa-miR-638, hsa-miR-642, hsa-miR-648, hsa-miR-652, hsa-miR-654, hsa-miR-657, hsa-miR-658, hsa-miR-659, hsa-miR-661, hsa-miR-662, hsa-miR-663, hsa-miR-664, hsa-miR-7, hsa-miR-7-1, hsa-miR-7-1*, hsa-miR-7-2, hsa-miR-7-3, hsa-miR-708, hsa-miR-765, hsa-miR-769-3p, hsa-miR-802, hsa-miR-885-3p, hsa-miR-9, hsa-miR-9-1, hsa-miR-9-3, hsa-miR-9*, hsa-miR-9-3p, hsa-miR-92, hsa-miR-92-1, hsa-miR-92-2, hsa-miR-9-2, hsa-miR-92, hsa-miR-92a, hsa-miR-93, hsa-miR-95, hsa-miR-96, hsa-miR-98, hsa-miR-99a and hsa-miR-99bmiR-145.

In some particularly preferred embodiments, the miRNA is selected from the group consisting of miR-17, miR-19, miR-21, miR-155, miR-196b, miR-92, miR-126 and miR-148a. Other preferred examples of heterologous MREs (and reference MREs) include those which are bound by (e.g. those whose nucleotide sequences are complementary to or partially complementary to) the above miRNAs.

These are miRNAs which are known to be differentially-expressed in human disease (e.g. Jiang Q. et al., "miR2Disease: a manually curated database for microRNA deregulation in human disease", Nucleic Acids Res. 2009 January; 37 (Database issue):D98-104. doi: 10.1093/nar/gkn714. Epub 2008 Oct. 15).

In some other preferred embodiments, the heterologous MRE and/or miRNA are selected from the following:

TABLE 1

Preferred miRNAs and their corresponding (perfect) MRE sequences

| miRNA name | microRNA sequence | Perfect MRE DNA sequence |
|---|---|---|
| miR-17 | 5'-CAAAGUGCUUACAGUGCAGGUAG-3' (SEQ ID NO: 1) | 5'-CTACCTGCACTGTAAGCACTTTG-3' (SEQ ID NO: 2) |
| miR-19 | 5'-UGUGCAAAUCUAUGCAAAACUGA-3' (SEQ ID NO: 3) | 5'-TCAGTTTTGCATAGATTTGCACA-3' (SEQ ID NO: 4) |
| miR-21 | 5'-UAGCUUAUCAGACUGAUGUUGA-3' (SEQ ID NO: 5) | 5'-TCAACATCAGTCTGATAAGCTA-3' (SEQ ID NO: 6) |
| miR-155 | 5'-UUAAUGCUAAUCGUGAUAGGGGU-3' (SEQ ID NO: 7) | 5'-ACCCCTATCACGATTAGCATTAA-3' (SEQ ID NO: 8) |
| miR-196b | 5'-UAGGUAGUUUCCUGUUGUUGGG-3' (SEQ ID NO: 9) | 5'-CCCAACAACAGGAAACTACCTA-3' (SEQ ID NO: 10) |

TABLE 1-continued

Preferred miRNAs and their corresponding (perfect) MRE sequences

| miRNA name | microRNA sequence | Perfect MRE DNA sequence |
|---|---|---|
| miR-92 | 5'-UAUUGCACUUGUCCCGGCCUGU-3' (SEQ ID NO: 11) | 5'-ACAGGCCGGGACAAGTGCAATA-3' (SEQ ID NO: 12) |
| miR-126 | 5'-UCGUACCGUGAGUAAUAAUGCG-3' (SEQ ID NO: 13) | 5'-CGCATTATTACTCACGGTACGA-3' (SEQ ID NO: 14) |
| miR-148a | 5'-UCAGUGCACUACAGAACUUUGU-3' (SEQ ID NO: 15) | 5'-ACAAAGTTCTGTAGTGCACTGA-3' (SEQ ID NO: 16) |

In one preferred embodiment, the MRE is that bound by miR-17-5p or miR-21.

Preferably, the nucleotide sequence of the heterologous MRE is selected such that the binding of the miRNA to the heterologous MRE results in or leads to a desired reduction of the level of expression of the gene.

In some embodiments, the nucleotide sequence of the heterologous MRE is selected such that the binding of the miRNA to the heterologous MRE results in or leads to total repression the gene. The heterologous MRE may also be a variant of a reference MRE.

As used herein, the term "reference MRE" refers to a MRE bearing perfect complementarity to every nucleotide of a given effector miRNA (in accordance with the rules of Watson-Crick base pairing). The reference MRE may, for example, be a naturally-occurring MRE. The heterologous MRE may be a modified MRE, e.g. a modified MRE derived from a reference MRE. In particular, the modified MRE may be a variant of one of the MREs described herein. (As used herein, the term "heterologous MRE" encompasses modified MREs).

The modified MREs generally have a high degree of sequence complimentary to a naturally-occurring miRNA. A general rule for making modified MREs is that introducing mismatches between the miRNA and the MRE generally reduced the potency of down-regulation. Making di-nucleotide mismatches generally reduces the potency of down-regulation in a manner that depends on the miRNA in question. In this way, the repression of gene expression can be tailored to a desired level.

In some embodiments, there are 1, 2, 3, 4, 5, 6, 7, 8, 9 or 10 nucleotide changes between the nucleotide sequences of the original/reference MRE and the modified MRE. In other embodiments, there are 1-10, 1-8, 1-5, 1-4, 1-3 or 1-2 nucleotide changes or only 1 change between the nucleotide sequences of the original/reference MRE and the modified MRE.

The changes are made to alter the binding affinity of the miRNA for the MRE and/or the efficiency of repression of the gene, preferably in a defined direction (i.e. to increase or to decrease the binding affinity of the miRNA for the MRE and/or the efficiency of repression of the gene).

The changes are independently selected from nucleotide substitutions, additions and deletions. Preferably, the changes are nucleotide substitutions. In some embodiments, non-natural nucleotides may be used.

Under appropriate conditions, the reference MRE and the modified MRE are both capable of being bound by a common miRNA. The nucleotide sequence of the modified MRE is designed such that the affinity and/or the efficiency of intra-cellular catalytic processing of the miRNA for the modified MRE are different to the affinity and/or the efficiency of catalytic processing of the miRNA for the reference MRE.

In general, the lower the level of affinity and/or the efficiency of catalytic processing between the miRNA and the modified MRE, the lower the level of repression of the associated gene.

As used herein, the term "heterologous MRE" refers to a MRE which does not occur naturally in the 3'-UTR of the gene into which it is being inserted.

For example, the heterologous MRE may be from the same organism (e.g. human) as the gene, but from a different gene in that organism. In other embodiments, the MRE is from a different organism from the gene.

Genes containing heterologous MREs can be identified as follows:

The sequence of a gene may be submitted to the National Center for Biotechnology Information BlastN suite
blast.ncbi.nlm.nih.gov/
Blast.cgi?PAGE=MegaBlast&PROGRAM=blastn&PAGE TYPE=BlastSearch&BLAST SPEC=OGP 10090 9559; see also Zheng Zhang et al. (2000), "A greedy algorithm for aligning DNA sequences", J. Comput. Biol. 2000; 7(1-2):203-14) and the host organism may be selected.

If the gene indeed contains a heterologous MRE, then BLAST will return two hits: one corresponding to the region of the gene upstream of the heterologous MRE and one corresponding to the region of the gene downstream of the heterologous MRE; and an unaligned gap which contains the heterologous MRE. FIG. 6 shows an example of such a BLAST output.

To confirm that the unaligned gap between the two hits indeed contains a heterologous MRE, the entire sequence may be submitted to a miRNA target-prediction tool such as PITA genie.weizrnann.ac.il/pubs/mir07/mir07 prediction-.html; see also Kertesz et al., "The role of site accessibility in microRNA target recognition", Nature Genetics 2007 [October; 39(10):1278-84. Epub 2007 Sep. 23).

To confirm that the unaligned gap between the two hits indeed contains a heterologous MRE, the entire sequence may be submitted to a miRNA target-prediction tool such as PITA (http://genie.weizmann.ac.il/pubs/mir07/mir07_prediction.html; see also Kertesz et al., "The role of site accessibility in microRNA target recognition", Nature Genetics 2007 [October; 39(10):1278-84. Epub 2007 Sep. 23).

If a heterologous MRE has indeed been inserted, PITA will predict a miRNA target site within the unaligned portion of the gene. The entire unaligned region can then be compared with the predicted miRNA to determine the type of heterologous MRE that it contains, whether perfect or modified. FIG. 7 gives an example of such a PITA output.

The heterologous MRE is inserted into the 3'-UTR of the gene. In this way, the RNA-encoding or protein-coding sequence of the gene and the heterologous MRE become physically linked, e.g. by a stretch of nucleotides, such that the RNA-encoding or protein-coding sequence and heterologous MRE are capable of being transcribed into a single RNA molecule or are present in a single RNA molecule.

As used herein, the term "inserting" includes introducing a nucleic acid molecule encoding the heterologous MRE into the 3'-UTR of the gene, for example by a genetic engineering technique.

As used herein, the term "inserting" also includes changing the nucleotide sequence of an existing MRE which is already present in the 3'-UTR of the gene to bring the nucleotide sequence of the existing MRE sequence into line with the sequence of a desired heterologous MRE.

The heterologous MRE may be inserted into one or both alleles (or more, if present) of the gene in the cell.

The insertion of the heterologous MRE may be performed by any suitable molecular biology technique or otherwise. For example, such techniques are described in "Molecular Cloning: A Laboratory Manual" (Fourth Edition) Michael R. Green and Joseph Sambrook. CRISPR-based techniques may also be used, such as those described in "CRISPR-Cas: A Laboratory Manual" (2016), edited by Jennifer Doudna (University of California, Berkeley) and Prashant Mali (University of California, San Diego). TALENs-based techniques may also be used.

In order to avoid disrupting existing gene-regulation with a cell, it is preferable to insert the heterologous MRE into the 3'-UTR in a MRE-desert. As used herein, the term "MRE-desert" refers to a region of the 3'-UTR which is free or is predicted to be free of MREs. The miRanda algorithm (34, 35) may be used to identify regions in the 3-UTR which are computationally-predicted to be free of MREs.

More than one heterologous MRE may be inserted into the gene. For example, the gene may comprise 2, 3, 4, or 5 heterologous MREs, which may be the same or different. Preferably, all of the heterologous MREs which are inserted are joined contiguously or are separated only by short stretches of nucleotides (e.g. 1-5 or 1-10 nucleotides).

As used herein, the term "modulating the level of expression of a gene" is intended to mean that the expression level of the gene is changed, i.e. increased or decreased, optionally by a defined, quantitated or semi-quantitated or undefined amount.

The levels of expression of the gene may be determined by any suitable means. Methods of determining expression levels include the use of qPCR, Western blot, flow-cytometry and ELISA involving the quantification of a relevant labelled-antibody.

The first and second expression levels should be determined under suitable comparable control conditions. For example, the control conditions may be a suitable cell-based system, e.g. one in which the genes, modified genes, RISC and miRNA in question (whichever need to be present in the relevant embodiment) are expressed.

The cell is one which expresses or is capable of expressing the gene of interest. In some embodiments, the cell is one which is expressing the gene.

In other embodiments, the cell is not one which is actively expressing the gene, but the cell is capable of expressing the gene under different conditions. For example, if the cell's internal or external conditions change, the cell may change from not expressing the gene to expressing the gene.

In embodiments wherein the cell is capable of expressing the gene (but is not expressing the gene at that time), the binding of the miRNA to the MRE results in or leads to a reduction of the level of expression of the gene (i.e. repression of the gene) when the gene is expressed.

Similarly, the cell is one which expresses the miRNA or is capable of expressing the miRNA of interest.

The cell is one which expresses or is capable of expressing a RISC complex. The RISC complex is capable of being loaded with a single strand from the miRNA and of recognising the MRE. In some embodiments, the cell is one which is expressing the miRNA.

In other embodiments, the cell is not one which is actively expressing the miRNA, but the cell is capable of expressing the miRNA under different conditions. For example, if the cell's internal or external conditions change, the cell may change from not expressing the miRNA to expressing the miRNA.

In embodiments wherein the cell is capable of expressing the miRNA (but is not expressing the miRNA at that time), the level of expression of the gene will be reduced when the miRNA is expressed and it binds to the MRE.

The cell is preferably a eukaryotic cell, more preferably a mammalian cell. Examples of mammalian cells include those from any organ or tissue from humans, mice, rats, hamsters, monkeys, rabbits, donkeys, horses, sheep, cows and apes. Preferably, the cell is a human cell.

The cell may be a totipotent or pluripotent cell, preferably a totipotent or pluripotent non-human mammalian cell or human cell. The cell may be a primary or immortalised cell. In some embodiments, the cell is not a human totipotent stem cell.

Preferred cell types include the following as well as the malignancies that arise from them: Embryonic Stem Cells (ESCs), Induced Pluripotent Stem Cells (iPSCs), Pluripotent Hematopoietic Stem Cells (HSC), Granulocyte Macrophage Progenitor Cells (GMP), Dendritic Cells (DC), Macrophages, Natural Killer T-cells (NKT), CD34+ cells, Thymocytes, CD8+ T-cells, CD4+ T-cells and B cells.

Preferred cell types also include the following primary malignant cells and immortalized cell cultures derived from them: Acute Lymphoblastic Leukaemia (ALL), Acute Myeloid Leukaemia (AML), Chronic Myelogenous Leukaemia (CML), Brain cancer, Breast Cancer, Carcinoma, Cervical Cancer, Colorectal Cancer, Bone Cancer, Gastric Cancer, Head and Neck Cancer, Hepatocellular Cancer, Leukaemia, Lung Cancer, Lymphoma, Melanoma, Osteosarcoma, Ovarian Cancer, Pancreatic Cancer, Prostate Cancer, Retinoblastoma, Sarcoma, Testicular Cancer and Thyroid Cancer.

The cells may be isolated cells, e.g. they are not currently present in a living animal.

The methods and processes of the invention may be performed in individual (e.g. isolated) cells or in populations of cells of the same or different type.

The MRE is one which is capable of being bound by the miRNA; the miRNA is expressed or is capable of being expressed in the cell. Cells expressing miRNAs will comprise a RNA-induced silencing complex, or RISC, which is a ribonucleoprotein, and which is capable of incorporating one strand of the miRNA. This strand acts as a template for RISC to recognize the MRE in the complementary mRNA transcript. Hence the heterologous MRE is one which is capable of being bound by the miRNA when part of the cell's RISC complex.

When the miRNA is loaded into RISC, it can bind to a cognate MRE with a certain binding affinity (measured in Kd). The extent and positions of base-pairing between the miRNA and the MRE also affects the ability of one of the proteins in RISC, called Argonaute 2, to slice the gene transcript (measured in Kcat). These two properties therefore dictate how well the gene transcript will ultimately be repressed. Hence the binding of the miRNA as part of the cell's RISC complex to the heterologous MRE results in or leads to a reduction in the level of expression of the gene.

The efficiency of repression (which will be dependent on the binding affinity and catalytic efficiency of the miRNA-RISC complex) can be measured directly or indirectly. For example, the efficiency of repression may be measured indirectly by determining the level of repression of an associated reporter gene (e.g. as illustrated in the Examples attached herein). The efficiency of repression needs to be measured in the presence of the miRNA and the heterologous MRE, and RISC complex. For example, the efficiency of repression may be measured in a cell-based system in which the miRNA is expressed.

The miRNA may bind to or act on a modified MRE with a second efficiency of repression.

The processes and methods of the invention may be carried out in vitro, in vivo or ex vivo. Preferably, the processes and methods of the invention are carried out in cell-based systems, e.g. in isolated cells. In some embodiments, the processes and methods of the invention are not carried out in live animals.

In some embodiments, a plurality of modified MREs have independently been derived from a common MRE, wherein the common MRE is capable of being bound by the miRNA with a first affinity, and wherein the modified MREs are capable of being bound by the miRNA with a plurality of different affinities.

As used herein, the term "plurality of nucleic acid molecules" includes 2-50, 2-40, 2-30, 2-20, 2-10 or 2-5 nucleic acid molecules.

The nucleic acid molecule may be DNA or RNA, preferably DNA. The nucleic acid molecule may be single-stranded or double-stranded. Preferably, the nucleic acid molecule is double-stranded DNA.

The invention also provides a plurality of vectors or plasmids, wherein the plurality of vectors or plasmids comprise the plurality of nucleic acid molecules of the invention. The vector may, for example, be an expression vector or lentiviral vector, which comprises a nucleic acid molecule of the invention, optionally together with one or more operably-associated regulatory sequences.

The gene may comprise a promoter. The nucleic acid molecules of the invention may additionally comprise a promoter which is operably linked with nucleic acid molecule. The promoter may be a constitutive (non-inducible) promoter. Examples of suitable promoters the CMV, SV40, PGK (human or mouse), HSV TK, SFFV, Ubiquitin, Elongation Factor Alpha, CHEF-1, FerH, Grp78, RSV, Adenovirus E1A, CAG or CMV-Beta-Globin promoter, or a promoter derived therefrom. Preferably, the promoter is the Cytomegalovirus immediate early (CMV) promoter, or a promoter which is derived therefrom, or a promoter of equal or increased strength compared to the CMV promoter.

In a further embodiment, there is provided a population of cells, wherein the population of cells comprises a plurality of nucleic acid molecules, vector or plasmid of the invention.

The nucleic acid molecules, vectors or plasmids may or may not be integrated into the host genome of the cell or the mitochondrial genome.

In some embodiments, the method of the invention is performed on an endogenous gene which is in a cell which can be used to make a transgenic animal.

In particular, the invention provides a process for producing a non-human transgenic animal, the process comprising the steps:
(i) inserting a heterologous MRE into the 3'-UTR of a gene in the genome of a totipotent or pluripotent non-human cell; and
(ii) culturing the cell under conditions such that the cell develops into a transgenic non-human animal.

The invention also provides a process for making a non-human animal which expresses an endogenous gene at a desired expression level in defined cells of the animal, the process comprising the steps:
(i) inserting a heterologous MRE into the 3'-UTR of the endogenous gene in the genome of a totipotent or pluripotent non-human animal cell; and
(ii) culturing the cell under conditions such that the cell develops into a transgenic non-human animal;
wherein the MRE is selected as being one which is capable of being repressed by miRNA which are expressed in the defined cells.

In some embodiments, the nucleotide sequence of the MRE has been selected (e.g. the sequence is a variant based on a reference MRE sequence) to reduce or increase the binding affinity and/or efficiency of repression between the miRNA and the MRE in order to obtain the desired expression level of the endogenous gene.

The genome may be the cell's genome or the mitochondrial genome. The totipotent or pluripotent cells are ones which are capable of developing, under appropriate conditions, into a transgenic non-human animal. Suitable culture conditions are well known in the art. Examples of such cells include fertilised or unfertilised ova, zygote and stem cells (e.g. Embryonic Stem Cells (ESCs) and Induced Pluripotent Stem Cells (iPSCs)).

The transgenic animal may be a non-human mammal, e.g. mice, rats, hamsters, monkeys, rabbits, donkeys, horses, sheep, cows or apes. The invention also provides a transgenic non-human animal which has been produced by a process of the invention.

A major advantage of the methods and processes disclosed herein is that, in addition to using constitutively-expressed miRNAs for constant gene silencing, it is also possible to achieve spatial-temporal control of gene silencing in response to tissue- or disease-specific miRNA expression. By placing an essential gene of interest under the control of a miRNA that is highly overexpressed in cancer, for example, it is possible to implement cell-autonomous cancer-detection and elimination.

"Biological sample" as used herein is a sample of biological tissue or fluid that contains miRNA. Biological samples may include sections of tissues such as biopsy and autopsy samples, frozen sections taken for histologic purposes, archiva samples, blood, plasma, serum, sputum, stool, tears, CSF, mucus, hair, skin, etc. Biological samples also include explants and primary and/or transformed cell cultures derived from subject's tissues. Preferably, the biological sample is sample of cells from the subject, e.g. from a diseased tissue or organ.

The subject is preferably a mammal such as a primate (e.g. chimpanzee or human), cow, dog, cat, a rodent (e.g. guinea pig, rat, mouse), rabbit, bird, reptile or fish. Livestock and domestic animals are also of interest.

In some embodiments, the sample is a sample from a cancerous tissue. Examples of cancerous tissues include tissues from prostate cancer, breast cancer, colorectal cancer, cervical cancer, bladder cancer, head and neck cancer, esophageal cancer, leukaemia, lung cancer, ovarian cancer, pancreatic cancer, renal cancer, stomach cancer, skin cancer, testicular cancer, uterine cancer, glioblastoma, Ewing sarcoma, soft tissue sarcoma, and lung fibrosis.

In yet a further embodiment, the invention provides a method for inhibiting the production of a disease-promoting activator by a cell, wherein the cell comprises a first gene which encodes an agent which initiates the disease, wherein the cell also comprises a second gene which encodes an activator which promotes proliferation of the disease, the method comprising the steps of:
  (a) modifying the nucleotide sequence of the second gene's 3'-UTR to introduce a MRE for a miRNA which is differentially upregulated in cells which comprise the first gene,
wherein the binding of the miRNA to the MRE represses the production of the activator, and thereby limiting proliferation of the disease.

In yet a further embodiment, the invention provides a method for prophylactically inhibiting the production of a disease-promoting activator by a cell, wherein the cell is at risk of comprising a first gene which encodes an agent which promotes the disease, wherein the cell also comprises a second gene which encodes an activator which promotes proliferation of the disease, the method comprising the steps of:
  (a) modifying the nucleotide sequence of the second gene's 3'-UTR to introduce a MRE for a miRNA which is differentially upregulated in cells which comprise the first gene,
wherein, in cells which comprise the first gene, the binding of the miRNA to the MRE represses the production of the activator, and thereby limiting proliferation of the disease.

One particular advantage of these methods is that the cells which produce the miRNA are specifically targeted, leaving other cells essentially unaffected.

The invention also provides a cell whose genome comprises an endogenous gene encoding an activator wherein the activator is one which is capable of promoting the proliferation of the cell, and wherein the nucleotide sequence of the gene encoding the activator comprises a heterologous MRE in the 3'-UTR.

Preferably, the heterologous MRE is one which is capable of being bound by a miRNA which is differentially upregulated if the cell comprises a disease-promoting agent.

Preferably, the heterologous MRE is one which is capable of being bound by a miRNA which is differentially upregulated in cells which comprise a disease-promoting agent or in diseased cells.

Preferably, the activator promotes the expression of a gene encoding a disease-promoting agent.

The invention also provides a cell whose genome comprises an endogenous gene which is capable of causing a disease, and wherein the nucleotide sequence of the gene comprises a heterologous MRE in the 3'-UTR. The endogenous gene which is capable of causing a disease may, for example, be the alpha-globin gene. In this way, thalassemia could be treated by putting an MRE into the 3'-UTR of the alpha-globin gene. Whilst this would not stop cells from proliferating, it would enable them to carry oxygen.

The invention also provides a non-human transgenic animal comprising a cell of the invention.

In particular, the invention provides a process for producing a non-human transgenic animal, the process comprising the steps:

(i) inserting a heterologous MRE into the 3'-UTR of a gene in the genome of a totipotent or pluripotent cell; and
  (ii) culturing the cell under conditions such that the cell develops into a transgenic animal;
wherein the gene encodes an agent which promotes proliferation of a disease.

Preferably, the heterologous MRE is one which is capable of being bound by a miRNA which is differentially upregulated in cells of the animal which express the gene, which are disease-promoting or which are diseased.

The disease-promoting agent may be any agent which promotes a disease. The agent may act directly on the cells or it may be a secreted agent which affects other cells or tissues within the subject. In some embodiments, the disease-promoting agent is one which is necessary for disease proliferation. Examples of disease-promoting agents include polypeptides and RNA molecules, particularly aberrant polypeptides and RNA molecules, such as those which are the result of a gene-mutation, chromosomal rearrangement or gene-fusion.

As used herein, the term "differentially upregulated" refers to a miRNA which is over-expressed in cells of the animal which express the gene, which are disease-promoting or which are diseased in comparison to control cells which do not express the gene, which are not disease-promoting or which do not promote the disease, respectively.

The agent may, for example, be a transcription factor, a fusion protein, chromatin modifier, or a pathogen, e.g. a bacteria or virus.

The disease (as referred to herein) may, for example, be a cancer. Examples of cancers include prostate cancer, breast cancer, colorectal cancer, cervical cancer, bladder cancer, head and neck cancer, esophageal cancer, leukaemia, lung cancer, ovarian cancer, pancreatic cancer, renal cancer, stomach cancer, skin cancer, testicular cancer, uterine cancer, glioblastoma, Ewing sarcoma, soft tissue sarcoma, and lung fibrosis.

Some examples of diseases and the corresponding upregulated miRNAs and disease-promoting agents are given in Table 2 below:

TABLE 2

| disease | upregulated miRNA | disease-promoting agent |
| --- | --- | --- |
| MLL | miR-196b | Myb protein |
| Beta Thalassemia | miR-451 | Haemoglobin alpha 1 |
| Kras driven cancer | miR-31 | HSF-1 |

In one preferred embodiment, the disease-promoting agent is the Myb transcription factor. Expression of the Myb protein promotes the proliferation of mixed lineage leukaemia (MLL).

The current invention has also been applied to the area of cancer immuno-therapy. The ability of cancer cells to evade the body's adaptive immune system often presents a hurdle to effective treatment (14). Expression of co-inhibitory ligands such as Programmed Death Ligand 1 (PD-L1) by tumour cells and antigen-presenting-cells in the tumor micro-environment serves as a "don't kill me" signal that allows cancers to escape immune-detection (15, 16). PD-L1 activates its cognate inhibitory surface receptor (PD-1) on effector T-cells, causing these immune cells to transition into an "exhausted" state that is characterized by diminished proliferative and cytotoxic potential. Monoclonal antibody drugs targeting the interaction between co-inhibitory receptors and their cognate ligands, collectively referred to as "checkpoint blockade" therapies, have shown promising clinical results across numerous cancer types (17-19).

Although patient response rates to checkpoint blockade therapies are high, the general up-regulation of effector T-cell activity comes with an increased risk of adverse autoimmune events (20). Establishing an optimal balance between T-cell exhaustion and autoimmune reactivity by fine-tuning the level of co-inhibitory receptor expression represents a critical challenge in this biomedical research space. By introducing a panel of MREs which are responsive to a miRNA which is highly expressed in activated T-cells, a range of PD-1 expression levels may be attained. The MREs may be introduced into the endogenous PD-1 locus using CRISPR/Cas9, an efficient, targeted genome-editing system (21).

Recently, CRISPR/Cas9 was used to catalyze efficient homology-directed repair in primary human T-cells (21). Purified Cas9 protein can be supplied in a complex with an sgRNA and a single stranded oligonucleotide homology donor (ssODN), and targeted insertions can thereby be generated in CD8+ human T-cells. A similar strategy may be used to engineer primary T-cells derived from mouse spleens, thus implementing a protocol that will parallel downstream clinical usage. In this way, pools of ex-vivo engineered T-cells containing several types of MREs can be assessed for their anti-cancer and autoimmune activity in vivo using, for example, a grafted mouse melanoma model.

In yet a further embodiment therefore, the invention provides a cell which expresses an immune checkpoint polypeptide, wherein the nucleotide sequence of the gene encoding the immune checkpoint polypeptide comprises a heterologous MRE in the 3'-UTR.

Preferably, the cell is a T-cell or a T-cell derived from a stem cell (e.g. an iPSC, an embryonic stem cell or a hematopoietic stem cell (HSC)). More preferably, the cell is a primary tumour infiltrating T-cell or an iPSC derived from a primary tumour infiltrating T-cell.

Preferably, the heterologous MRE is one which is capable of being bound by a miRNA which is differentially upregulated in activated T-cells.

Preferably, the activated T-cells are ones which have been activated following binding of a ligand to the immune checkpoint polypeptide.

In this embodiment, the heterologous MRE is preferably one which is capable of being bound by a miRNA which is differentially upregulated in activated T-cells.

Preferably, the original T-cells are from a mammal, e.g. a human, mouse, rat, or non-human primate. Preferably, the T-cells are effector T-cells, regulatory T-cells, helper T-cells or antigen presenting cells such as dendritic cells or macrophages.

Immune checkpoint polypeptides are molecules in the immune system that either turn up a signal (co-stimulatory molecules) or turn down a signal. Many cancers protect themselves from the immune system by inhibiting the T-cell signal. The immune checkpoint polypeptides may be stimulatory or inhibitory. For example, the immune checkpoint polypeptide may be stimulatory polypeptide which it is desired to down-regulate in order to help to prevent an autoimmune disease.

Examples of inhibitory immune checkpoint polypeptides include the following: A2AR. The Adenosine A2A receptor is regarded as an important checkpoint in cancer therapy because adenosine in the immune microenvironment, leading to the activation of the A2a receptor, is negative immune feedback loop and the tumour microenvironment has relatively high concentrations of adenosine.

B7-H3, also called CD276, was originally understood to be a co-stimulatory molecule but is now regarded as co-inhibitory.

B7-H4, also called VTCN1, is expressed by tumour cells and tumor-associated macrophages and plays a role in tumour escape.

BTLA. This molecule, short for B and T Lymphocyte Attenuator and also called CD272, has HVEM (Herpesvirus Entry Mediator) as its ligand. Surface expression of BTLA is gradually downregulated during differentiation of human CD8+ T cells from the naive to effector cell phenotype. However, tumor-specific human CD8+ T cells express high levels of BTLA.

CTLA-4 is short for Cytotoxic T-Lymphocyte-Associated protein 4; it is also called CD152. Expression of CTLA-4 on Treg cells serves to control T cell proliferation.

IDO, short for Indoleamine 2,3-dioxygenase, is a tryptophan catabolic enzyme with immune-inhibitory properties. Another important molecule is TDO, tryptophan 2,3-dioxygenase. IDO is known to suppress T and NK cells, generate and activate Tregs and myeloid-derived suppressor cells, and promote tumour angiogenesis.

KIR, short for Killer-cell Immunoglobulin-like Receptor, is a receptor for MHC Class I molecules on Natural Killer cells.

LAG3, short for Lymphocyte Activation Gene-3, works to suppress an immune response by action to Tregs as well as direct effects on CD8+ T-cells.

PD-1, short for Programmed Death 1 (PD-1) receptor, has two ligands, PD-L1 and PD-L2. An advantage of targeting PD-1 is that it can restore immune function in the tumour microenvironment.

TIM-3, short for T-cell Immunoglobulin domain and Mucin domain 3, expresses on activated human CD4+ T-cells and regulates Th1 and Th17 cytokines. TIM-3 acts as a negative regulator of Th1/Tc1 function by triggering cell death upon interaction with its ligand, galectin-9.

VISTA (C10orf54) is short for V-domain Ig suppressor of T-cell activation. VISTA is primarily expressed on hematopoietic cells so that consistent expression of VISTA on leukocytes within tumors may allow VISTA blockade to be effective across a broad range of solid tumors.

Preferably, the immune checkpoint polypeptide is PD-1. PD-1 has two ligands, PD-L1 and PD-L2, which are members of the B7 family. PD-L1 protein is upregulated on macrophages and dendritic cells (DC) in response to LPS and GM-CSF treatment, and on T-cells and B-cells upon TCR and B-cell receptor signaling, whereas in resting mice, PD-L1 mRNA can be detected in the heart, lung, thymus, spleen, and kidney. PD-L1 is expressed on almost all murine tumor cell lines, including PA1 myeloma, P815 mastocytoma, and B16 melanoma upon treatment with IFN-γ. PD-L2 expression is more restricted and is expressed mainly by DCs and a few tumor lines. Preferably, the ligand is PD-L1.

Examples of miRNA which are upregulated in activated T-cells include miR-146a, miR-152-3p, miR-27a, miR-10a, miR-155. Preferably, the miRNA is miR-21.

It is currently believed that inhibitory immune checkpoint polypeptides negatively regulate T-cell responses.

On the one hand, therefore, the repression of a gene encoding an inhibitory immune checkpoint polypeptide (e.g. PD-1) by an appropriate miRNA (e.g. miR-21) can lead to a reduction in the negative regulation of the T-cell response. On the other hand, however, the total elimination of the negative regulation of the T-cell response can lead to upregulation of T-cell activity, which brings with it an increased risk in adverse autoimmune events.

The repressive activity of the miRNA for the modified MRE is therefore preferably selected to provide an appropriate balance between these two effects.

Thus in one embodiment, the repressive activity of the miRNA on the modified MRE is selected such that the T-cell, in the presence of the miRNA, is not deactivated or the activity of the T-cell is not negatively regulated upon contact with a cell expressing a ligand for the immune checkpoint polypeptide. Preferably, the T-cell, in the presence of the miRNA, possesses some anti-cancer cell activity.

Preferably, the repressive activity of the miRNA on the modified MRE is also selected such that the activity of the T-cell, in the presence of the miRNA, is not up-regulated to the extent that the T-cell attains an autoimmune capacity against one or more normal tissues.

In yet a further embodiment, the invention provides a method of producing a modified cell, the method comprising the step of:

(a) in the genome of a cell, inserting the nucleotide sequence of a heterologous MRE into the 3'-UTR of a gene which encodes an immune checkpoint polypeptide.

Preferably, the cell is a T-cell, or a T-cell derived from a stem cell (e.g. an iPSC derived from a T-cell, an embryonic stem cell or a hematopoietic stem cell (HSC)). More preferably, the cell is a primary tumour infiltrating T-cell or an iPSC derived from a primary tumour infiltrating T-cell.

Preferably, the heterologous MRE is one which is capable of being bound by a miRNA which is differentially upregulated in activated T-cells. Preferably, the heterologous MRE is one which is capable of being bound by a miRNA which is differentially upregulated in tumour infiltrating T-cells.

In yet a further embodiment, the invention provides a method of producing a plurality of modified cells, the method comprising the steps of:

(a) in the genomes of a plurality of cells, inserting the nucleotide sequences of heterologous MREs in the 3'-UTRs of genes which encode a common immune checkpoint polypeptide, thereby producing a plurality of cells each of which comprises a different heterologous MRE.

The nucleotide sequences of the common immune checkpoint polypeptides are the same (or essentially the same) apart from the different MREs.

Preferably, the method includes one or both of the additional steps of:

(b) selecting for cells having a heterologous MRE wherein, in the presence of the miRNA, the cell is not deactivated or the activity of the cell is not negatively regulated upon contact with a cell expressing a ligand for the immune checkpoint polypeptide. Preferably, the cell, in the presence of the miRNA, possesses some anti-cancer cell activity; and (c) selecting for cells having a heterologous MRE wherein, in the presence of the miRNA, the cell is not up-regulated to the extent that the cell attains an autoimmune capacity against one or more normal tissues.

Preferably, the cell is a T-cell, or a T-cell derived from a stem cell (e.g. an iPSC derived from a T-cell, an embryonic stem cell or a hematopoietic stem cell (HSC)). More preferably, the cell is a primary tumour infiltrating T-cell or an iPSC derived from a primary tumour infiltrating T-cell. Such selection may be carried out using a grafted mouse melanoma model, for example.

In yet a further embodiment, the invention provides a method of treating cancer cells in a subject, wherein the cancer cells have the potential of being detected by the immune system, the method comprising the steps of:

(a) in the genome of a T-cell which has been obtained from the subject, inserting the nucleotide sequence of a heterologous MRE in the 3'-UTR of a gene which encodes an immune checkpoint polypeptide thus producing a modified T-cell, wherein the heterologous MRE is one which is capable of being bound by a miRNA which is differentially upregulated in activated T-cells; and (b) introducing the modified T-cell into the subject;

wherein the modified T-cell, when activated by contact with the cancer cells, is not negatively regulated by the cancer cells, and wherein the modified T-cell promotes the destruction or rejection of the cancer cells. Preferably, the T-cells are effector T-cells. The cancer may be one disclosed herein.

In some embodiments, the cancer cells are ones which display a ligand for an immune checkpoint polypeptide which is capable of negatively-regulating effector T-cells.

The disclosure of each reference set forth herein is incorporated herein by reference in its entirety.

BRIEF DESCRIPTION OF THE FIGURES

FIG. 1: Altering MRE sequence identity modulates reporter gene expression: A) Sequence composition of 11 miRheos containing either one or two miR-17-5p target sites. The region complimentary to the miR-17-5p "seed" is highlighted in grey. Where applicable, mismatches are shown in bold and a short spacer sequence is shown in grey. B) Normalized EGFP expression 24 hours after miRheo transfection. Error bars represent SD of three independent transfections. C) Fluorescent microscopy of miRheo-regulated EGFP expression 24 hours post transfection.

FIG. 2: A three-reporter system for titrating miRNA-expression: A) Maps of p-Sensor-X and p-Titre-miR-21. B) Histogram of EYFP fluorescence 24 hours after transfection of 5 ng p-Titre-miR-21. C) Comparison of miR-21 copy number in cells transfected with p-Titre-miR-21 and sorted based on EYFP fluorescence. miR-21 RNA was reverse transcribed with a sequence-specific structured primer. Error bars show SD of absolute RT-ddPCR quantification across three independent populations. D) Flow-cytometry analysis of HEK 293 T cells 24 hours after co-transfected of p-Sensor-X and p-Titre-miR-21.

FIG. 3: Modeling miRheo-mediated gene-tuning in vitro: A and B) RT-ddPCR of naïve and stimulated (25 nM SIINFEKL) OT-1 splenocytes using miR-21 specific RT primer/probe set represented. Error bars (B) show SD of three independent biological samples. C) Sequences composition of 5 miR-21-specific miRheos. D) Normalized ECFP expression measured by flow-cytometry of miR-21 miRheos and a miR-67 (not expressed in mammals) control miRheo. Error bars show SD of three independent transfections. E) Cells are computationally binned on iBlue fluorescence, a proxy for un-repressed transcript abundance. E) Cells are computationally binned on EYFP, a proxy for miR-21 concentration. Points in (E, F) are shaded by miRheo type as in (D) and represent the mean of three independent transfections. G) Schematic map of reporter constructs bearing the PD1-3'UTR downstream of EGFP. Positions where miR-21 MREs were cloned into each construct are indicated. H) EGFP expression measured by flow-cytometry for reporter constructs bearing miR-21

MREs in the positions specified in (G). Error bars reflect standard deviation of three independent transfections.

FIG. 4: A strategy for fine-tuning PD-1 expression in T-cells: A) A Cas9-mediated HDR strategy for introducing MREs into the endogenous PD1 3'UTR. Transcripts from edited loci are downregulated by miR-21. B and C) Restriction enzyme-based genotyping OT1 ES cells (B) or primary T cells (C) co-transfected with an sgRNA targeting the Myb 3'UTR and an HDR bearing a BamHI site D) Three strategies for introducing miRheos into the endogenous PD-1 3'UTR.

FIG. 5: Synthetic MREs regulate MYB expression in a miRNA-dependent manner: A) miRNA expression in bone marrow retrovirally transduced with either MLL-AF9 (dark grey) or an empty vector control (light grey) measured by nCounter. B) High-resolution melt analysis on genomic DNA from B16F10 cells transfected with an sgRNA targeting the Myb 3'UTR. Normalized, temperature adjusted melt (top) and difference (bottom) curves are shown for a 220 bp amplicon spanning the predicted Cas9 cut site. C) A Cas9-mediated HDR strategy for introducing MREs into the endogenous MYB 3'UTR. Transcripts from edited loci are downregulated by miR-196b. D) PCR-based genotyping of gDNA derived from 96 single-cell mESC clones edited using the strategy shown in (C). E) MiSeq reads aligned to an artificial reference genome containing perfectly modified and WT MYB loci. Each horizontal track represents de-multiplexed reads from a single mESC clone. F) RT-qPCR of mESCs nucleofected with a miR-196-b mimic. qPCR was performed by I-Jun Lau. G) Strategies for generating and testing transgenic, MRE-bearing mice. H) PCR genotyping of F1 mice to confirm MRE insertion in the MYB 3'UTR.

FIG. 6: An example of a BLAST output illustrating how heterologous MREs may be identified.

FIG. 7: An example of a PITA output, predicting MRE sites within a gene.

EXAMPLES

The present invention is further illustrated by the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Production of Panel of Mutated MREs

We designed a panel of mutated MREs comprised of one or two miRNA target sites. Each target site contains one of several di-nucleotide mismatches to an effector miRNA (miR-17-5p) endogenously expressed in HEK 293 T, an immortalized human cell line (FIG. 1A).

We created a bi-directional expression construct containing a fluorescent reporter (EGFP) and an internal copy-number control (iBlue). We appended degradation tags to both fluorophores to promote rapid turnover kinetics and named the resulting construct p-Sensor-X.

Figure 1B:
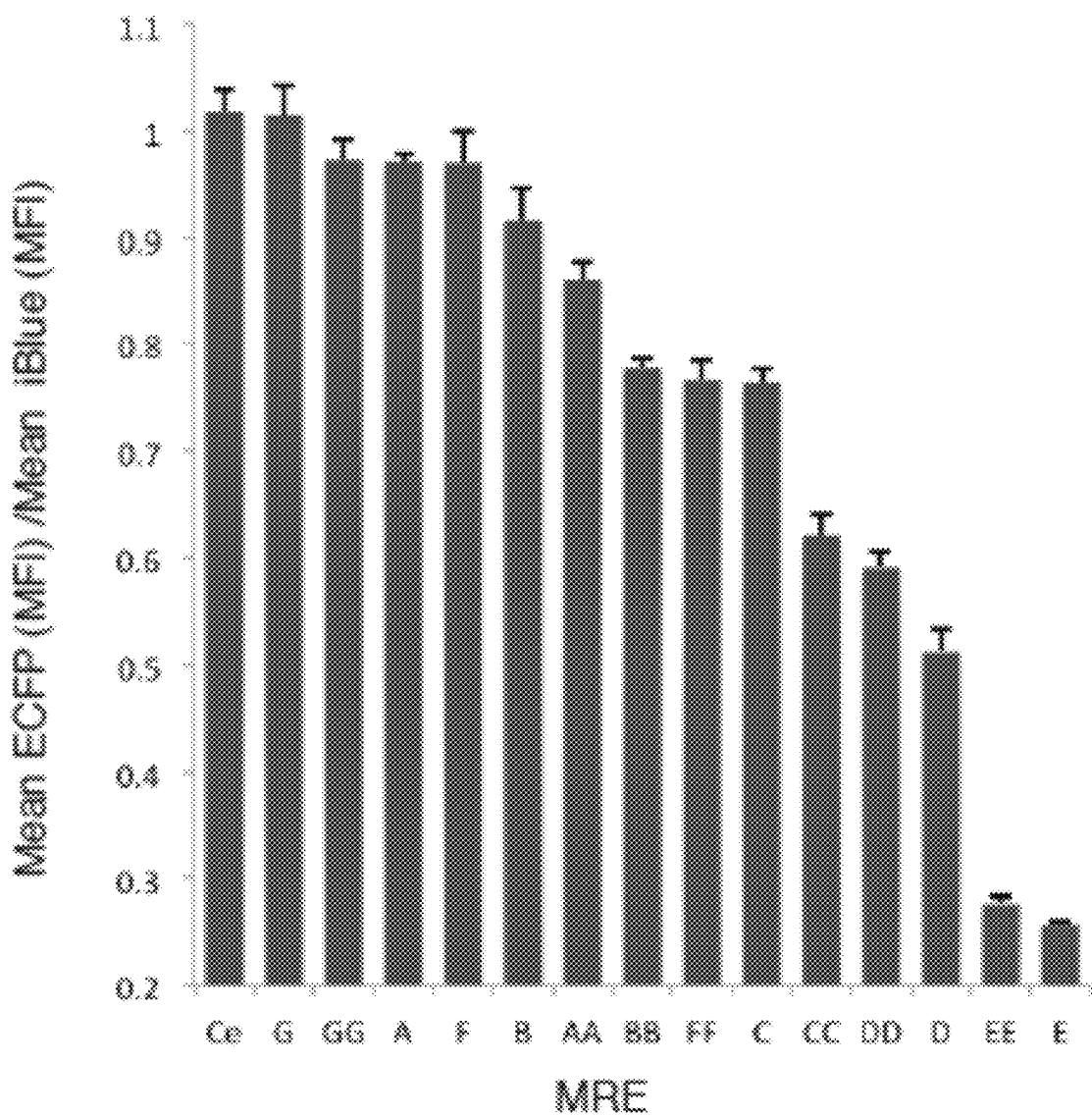
Figure 1C:
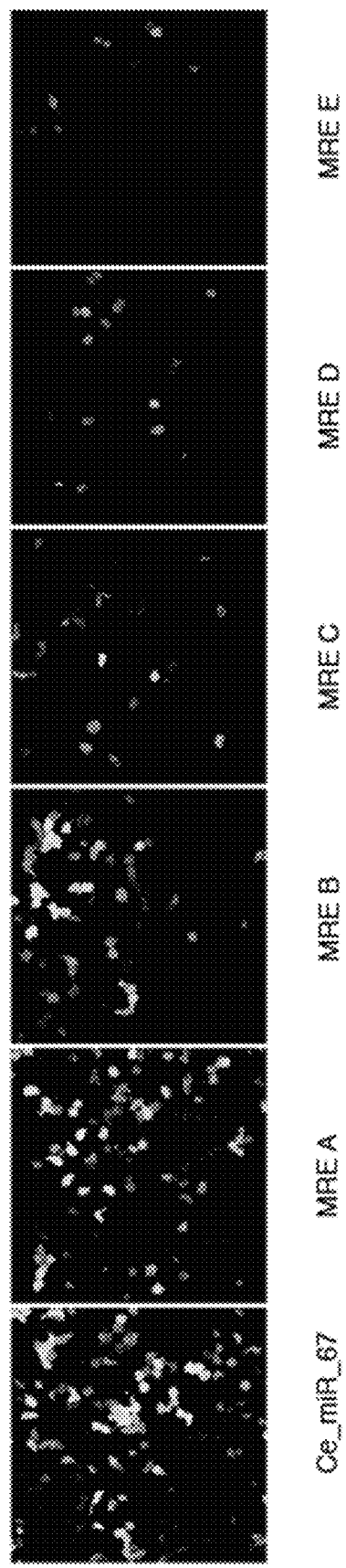

Next we cloned 15 different MREs into the 3'UTR of EGFP. We transiently transfected HEK-293T cells with these constructs and assayed reporter fluorescence by flow cytometry (FIG. 1B) and microscopy (FIG. 1C). As predicted, these MREs elicited various levels of EGFP expression ranging from ~5% to ~90% of an un-silenced control, providing a suitable panel of miRheos for further experimentation.

Example 2

Quantification of miRNA Expression

Successful implementation of miRheos in downstream biological applications would greatly benefit from the ability to model MRE-mediated gene silencing across variable miRNA-target stoichiometry (7). To this end, we expanded our fluorescent reporter system to include a second bi-directional expression plasmid, which we call p-Titre-miR, that delivers a miRNA in tandem with EYFP, a fluorescent copy-number control (FIG. 2A). We reasoned that cells expressing higher levels of EYFP would have concordantly higher levels of miR-21, allowing us to assess the effect of miRNA copy number on MRE-mediated repression at single-cell level.

We cloned the miR-21 primary transcript into p-Titre-miR and transiently transfected the resulting construct into HEK-293T cells. We sorted cells on EYFP fluorescence (FIG. 2B) and quantified miR-21 by digital droplet PCR (ddPCR) (FIG. 2C). Over the range assayed, miR-21 copy number correlates linearly with EYFP fluorescence ($R^2=1$, $p<0.001$, $n=3$ transfection replicates). Next we verified that p-Titre-miR-21 represses p-Sensor-X in a sequence specific manner without perturbing the internal transfection control (FIG. 2D).

Example 3

Modeling Gene Repression as a Function of miRNA Expression

Figure 3A:
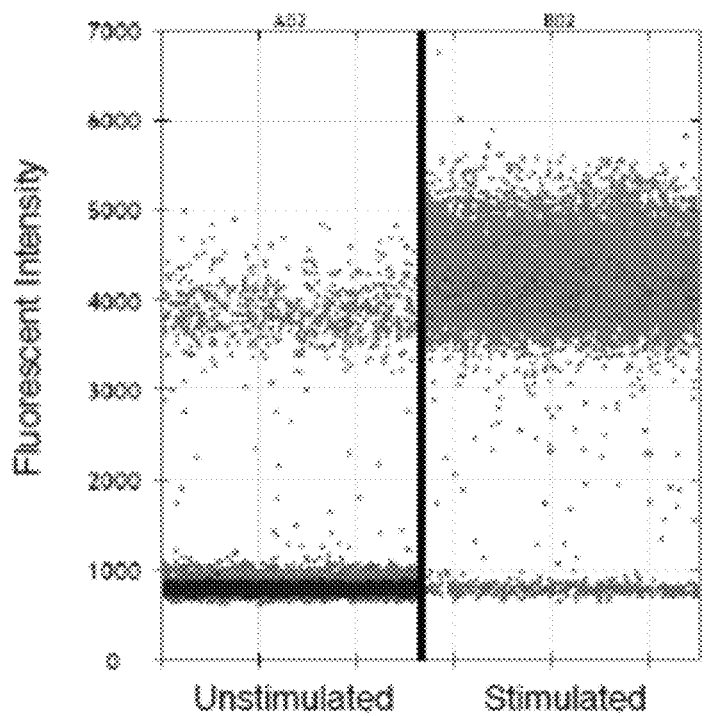
Figure 3B:
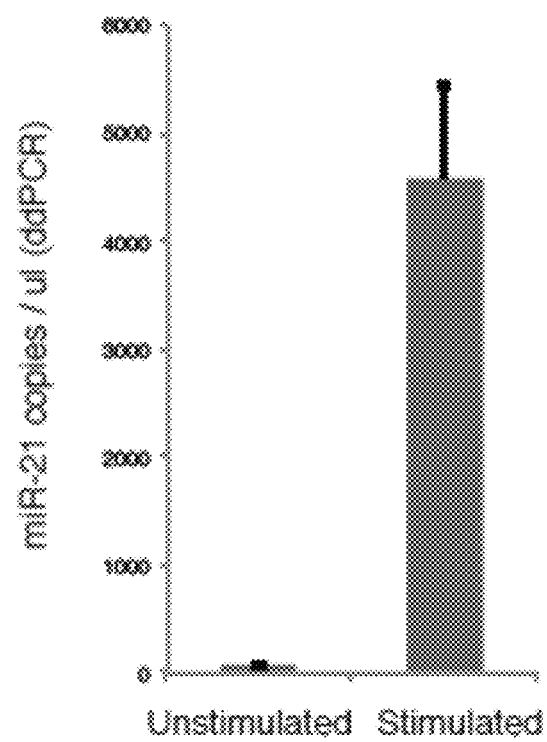

Since we aim to apply miRheos towards fine-tuning co-inhibitory receptor expression in activated CD8$^+$ effector T cells, we searched for a constitutively-expressed effector-miRNA in this cell type. Several previous screens have detected high levels of miR-21 expression in activated human and mouse CD8$^+$ T-cells (30-32). To validate these findings, we extracted spleens from OT-1 mice, a strain engineered to recognize the ovalbumin antigen (33). We activated primary splenocytes with a short ovalbumin peptide and extracted total RNA at 48 hours post activation. Reverse transcription, ddPCR (RT-ddPCR) confirmed massive miR-21 up-regulation following activation (FIG. 3A, B).

Figure 3C:
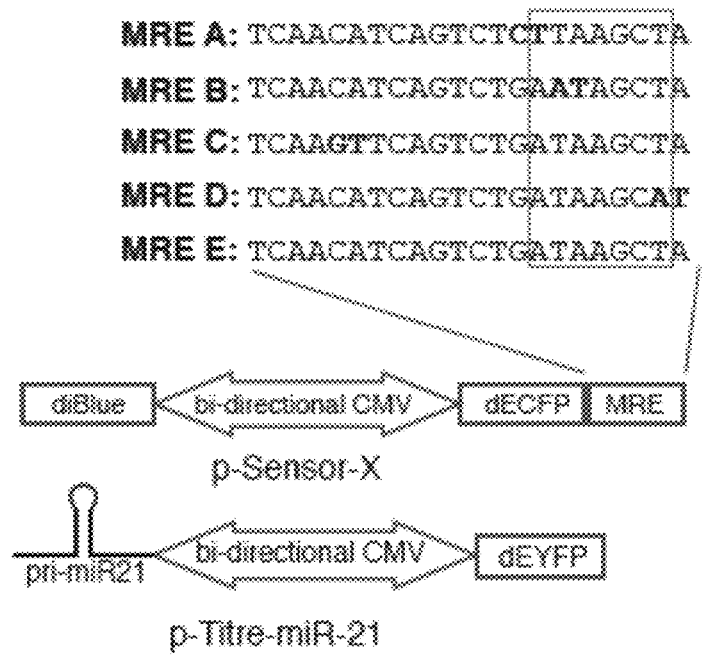
Figure 3D:
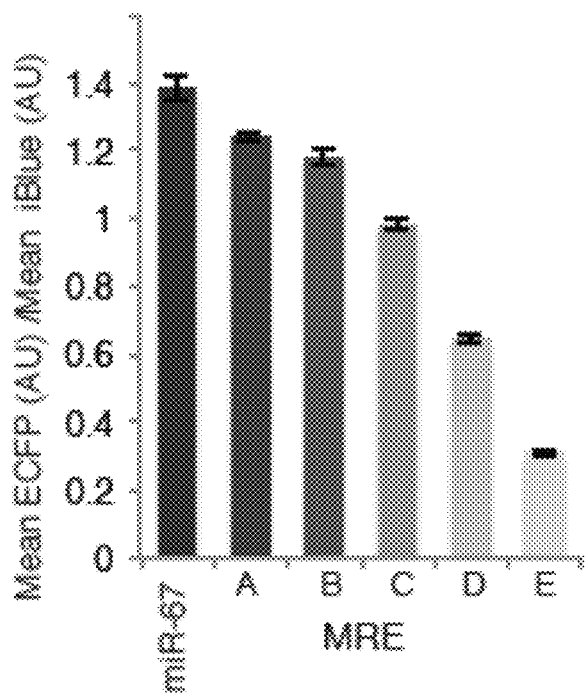
Figure 3F:
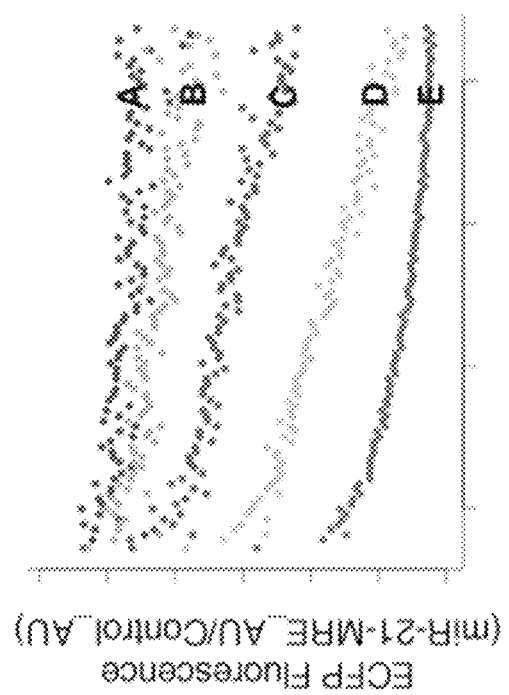
Figure 3E:
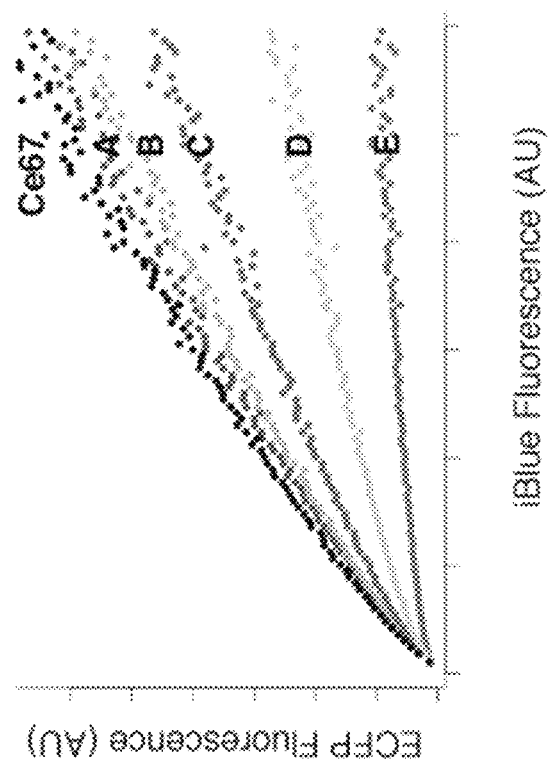

Next we used the three-color fluorescent reporter system to model the activity of five miR-21 miRheos across a range of miRNA and target gene expression levels (FIG. 3C). We co-transfected HEK-293T with p-Titre-miR-21 along with p-Sensor constructs containing each miRheo, and observed a large dynamic range of silencing by flow cytometry. Next, we computationally-binned cells on iBlue, a proxy for unrepressed mRNA copy number (FIG. 3E) and EYFP, a readout for miRNA copy number (FIG. 3F). All MREs appeared to obey Michaelis-Mentin kinetics, consistent with catalytic transcriptional repression (7, 11, 13). The relative order of reporter silencing is preserved across all mRNA and miRNA levels assayed, validating the versatility of miRheos.

Example 4

Applying miRheos Towards Checkpoint Blockade Therapy

Next we sought to introduce miR-21 responsive miRheos into the endogenous PD-1 3'UTR in effector T-cells. We reasoned that by supplying the Cas9 protein along with a sgRNA targeting the PD-1 3'UTR and an ssODN carrying the miRheo, we could efficiently introduce miRheos into the genome by homology-directed repair (HDR).

Figure 3G:
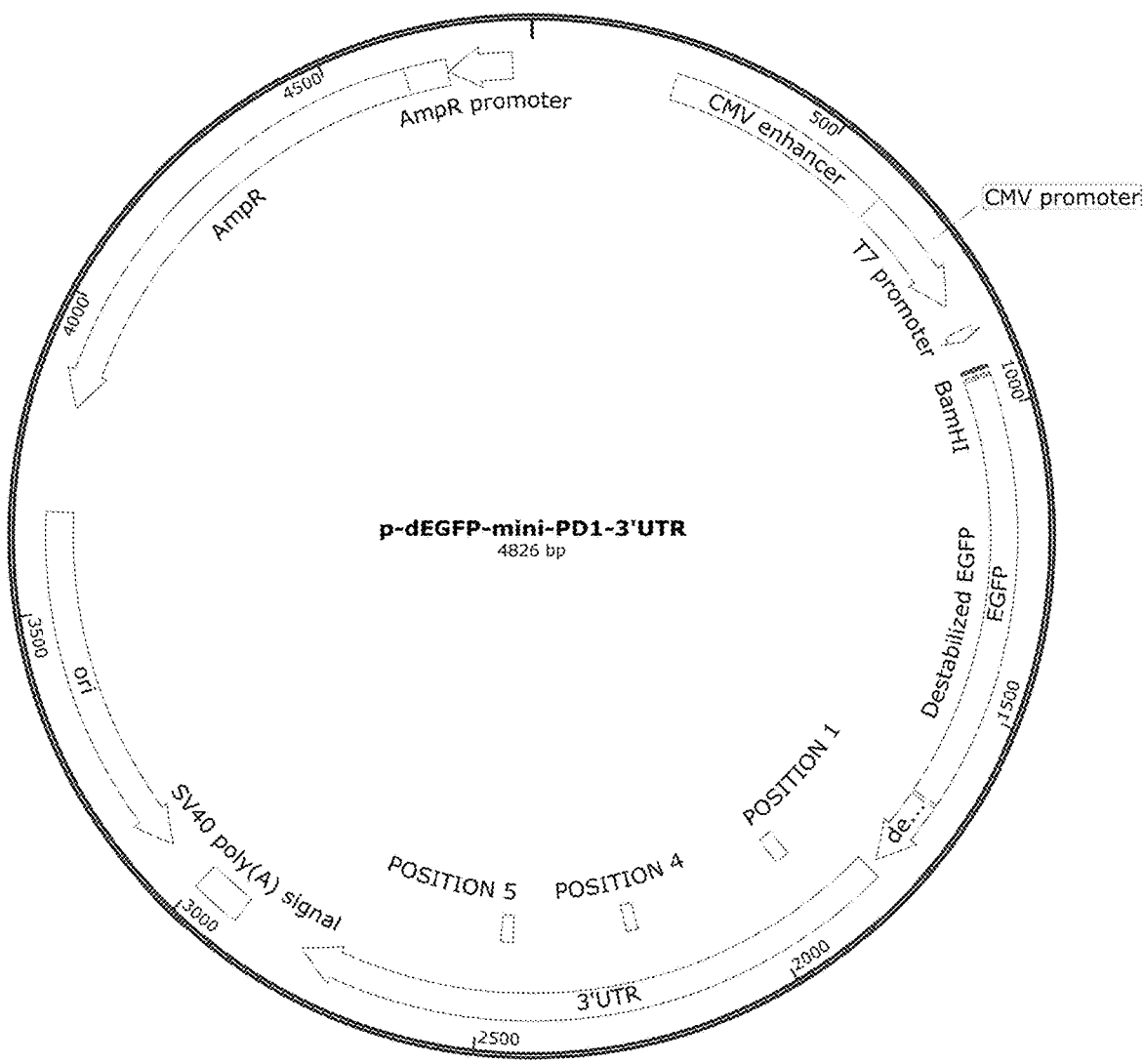
Figure 3H:
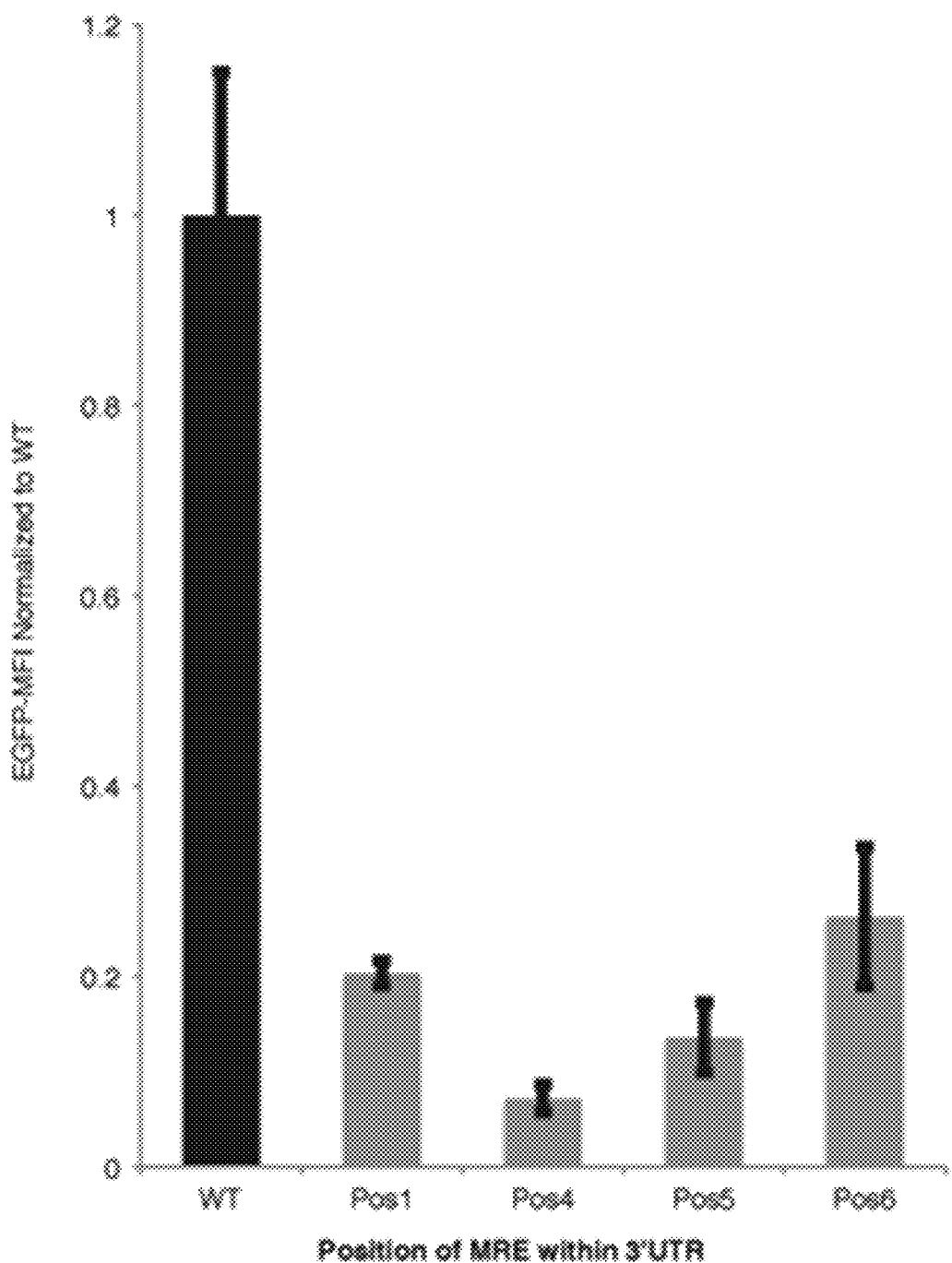
Figure 4A:
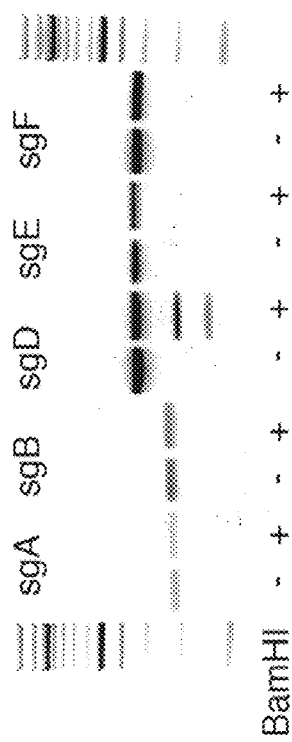

We began by designing candidate sgRNAs for the PD-1 3'UTR. To avoid disrupting existing gene-regulation, we used the miRanda algorithm (34, 35) to identify regions in the 3'UTR free of computationally-predicted MREs. We reasoned that secondary structure, RNA binding protein motifs or other sequence features may render some regions of the PD1 3'UTR unsuitable for MRE mediated gene silencing. To explore this possibility, we generated a reporter construct comprising the PD1 3'UTR downstream of EGFP. We inserted a miR-21 MRE at several 'VIRE desert' regions in the 3'UTR (FIG. 3G). These positional variants were transiently transfected into HEK 293t cells and MRE functionality was monitored by flow cytometry. We observed strong repressive activity for each positional variant tested indicating that the PD1 3'UTR is broadly amenable to heterologous MRE regulation (FIG. 3H). Next, we submitted these 'VIRE desert' regions to two sgRNA-design algorithms (36, 37) and selected five sgRNAs on the basis of predicted on-target and off-target activity. We cloned the target sequences into pX459 (a vector that simultaneously drives expression of NLS-spCas9, sgRNA and puromycin-resistance gene). We transfected these plasmids as well as a homology donor containing a BamH-I site into mouse embryonic stem cells (mESCs) (FIG. 4A). After a 48 hour purmoycin, we extracted genomic DNA, PCR amplified the targeted locus and digested with BamH-I to assess HDR efficiency (FIG. 4B) (38).

Figure 4B:
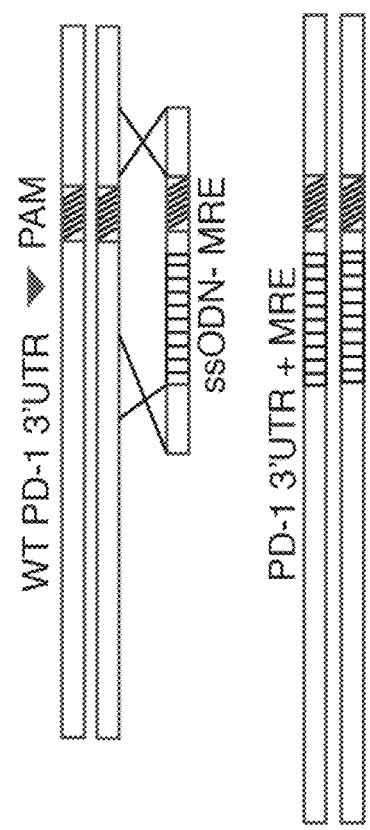
Figure 4C:
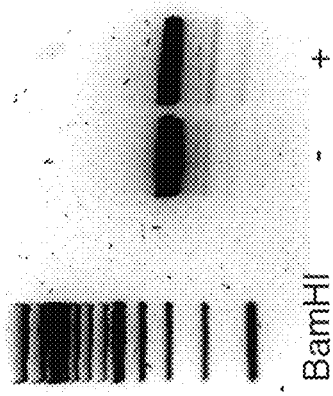
Figure 4D:
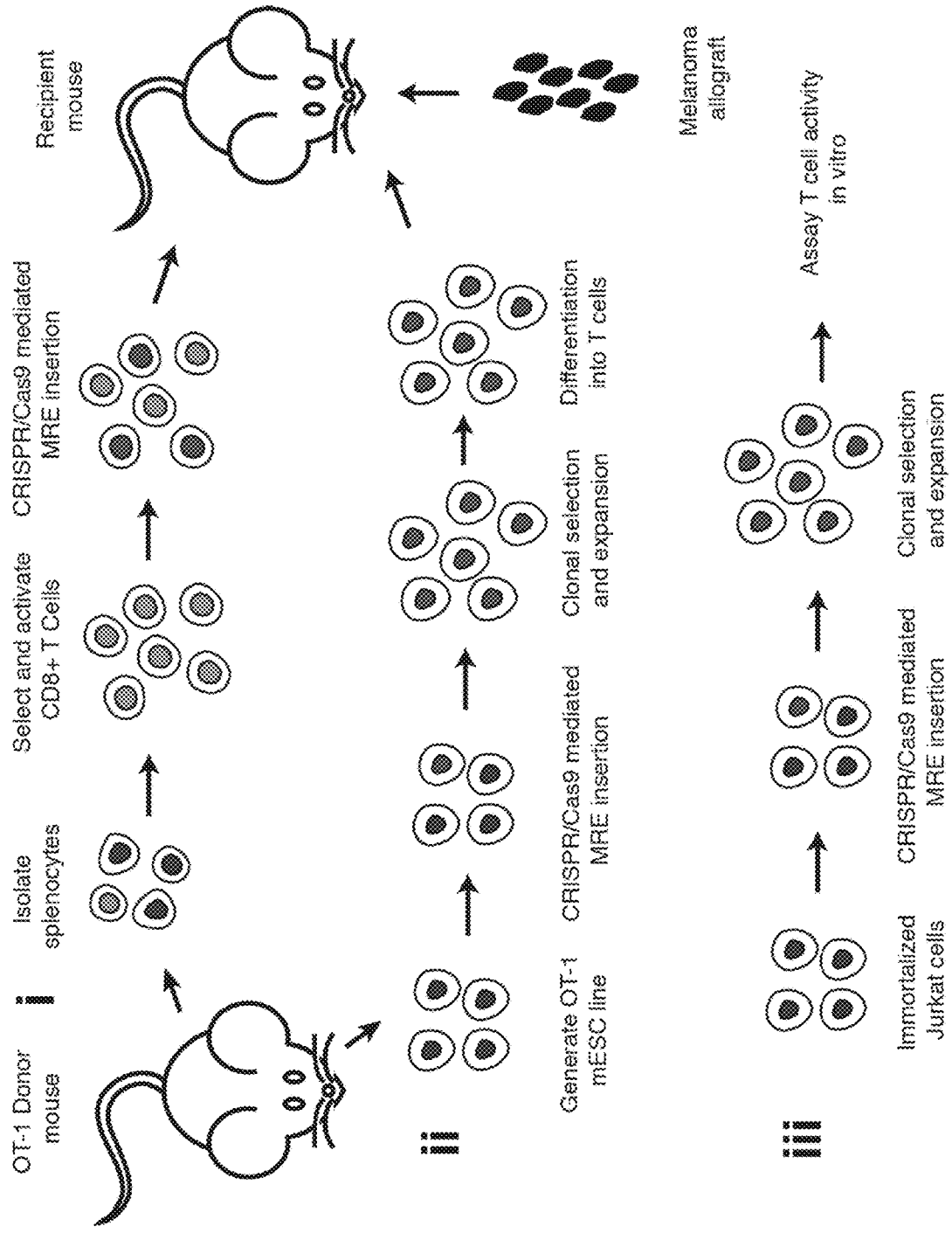

One guide RNA showed good HDR efficiency in mESCs (FIG. 4B). We next attempted to engineer primary CD8+ T-cells. We extracted splenocytes from OT-1 mice, a strain specific for the ova-albumin antigen. We activated naïve OT-1 T-cells with SIINFEKL (25 nM), a short peptide from ova-albumin. 24 hours post-activation, we nuclefected cells with in vitro transcribed sgRNA-D, a homology donor carrying a BamH-I site and Cas9 protein labeled with Alexa488 (48). 24 hours post-transfection, we used FACS to enrich for Alexa 488 positive, transfected cells. After 24 hours in culture, we harvested cells, PCR amplified the targeted locus and digested with Bam-HI to assess HDR efficiency (FIG. 4C). We observed detectable, albeit inefficient HDR. To overcome the limitation of poor HDR efficiency, an alternative approach is to engineer mESCs, select and expand correctly modified clones and differentiate these MRE-bearing cells into T-cells.

Example 5

Creating a Safety Switch for MLL-AF9 Leukemia

Figure 5A:
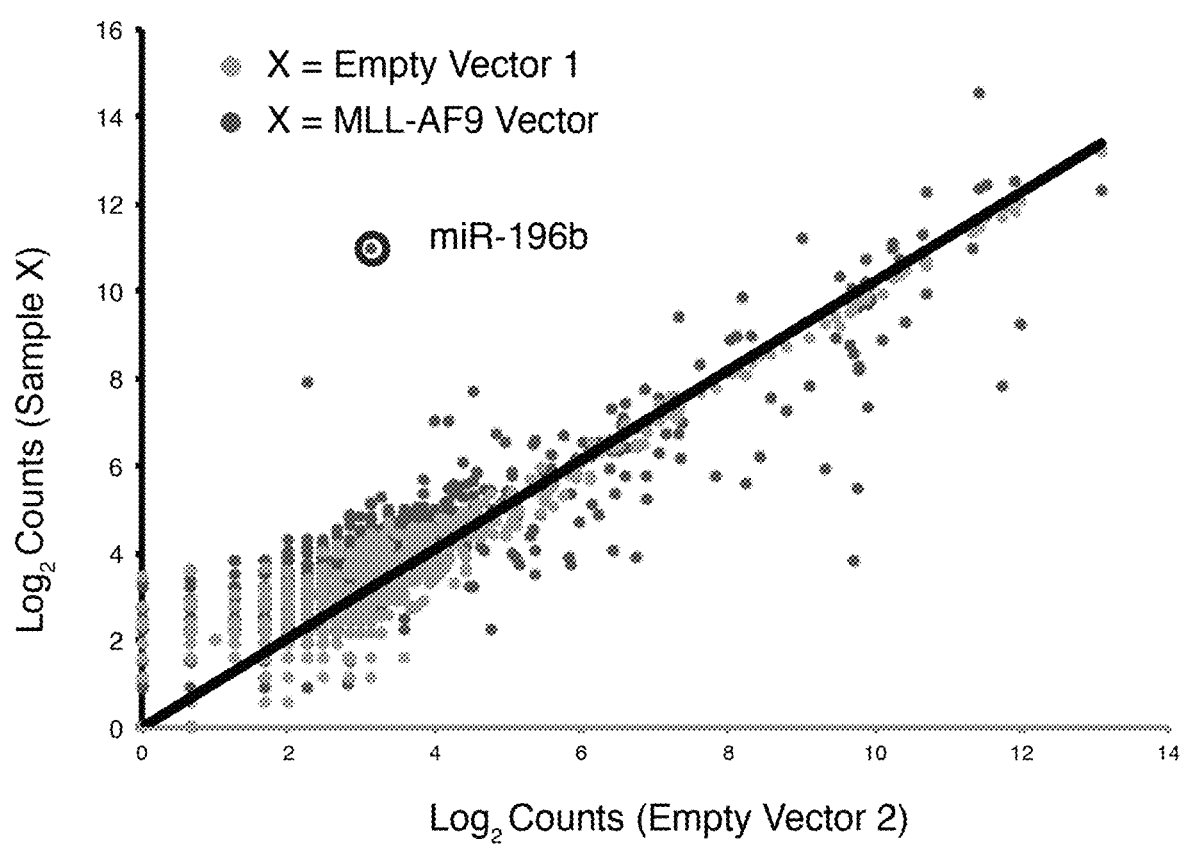

An additional application of synthetic MREs is detection of disease-specific miRNA expression in a cell-autonomous fashion. We sought to implement such a system in a murine model of MLL-AF9 leukemia. Primary bone marrow was retrovirally transduced, either with a vector carrying a puromycin resistance cassette alone (empty vector), or a virus carrying the puromycin resistance cassette plus the MLL-AF9 fusion gene (MLL-AF9 vector). We extracted total RNA and profiled miRNA expression using the NanoString nCounter Analysis System (FIG. 5A). Several miRNAs appeared to be differentially expressed between the empty vector and MLL-AF9 samples; most notably, miR-196b displayed over 200 fold upregulation in the MLL-AF9 sample. This was consistent with previous miRNA expression profiles in mouse models and patient samples of MLL-AF9 leukemia (26, 27, 39).

Figure 5B:
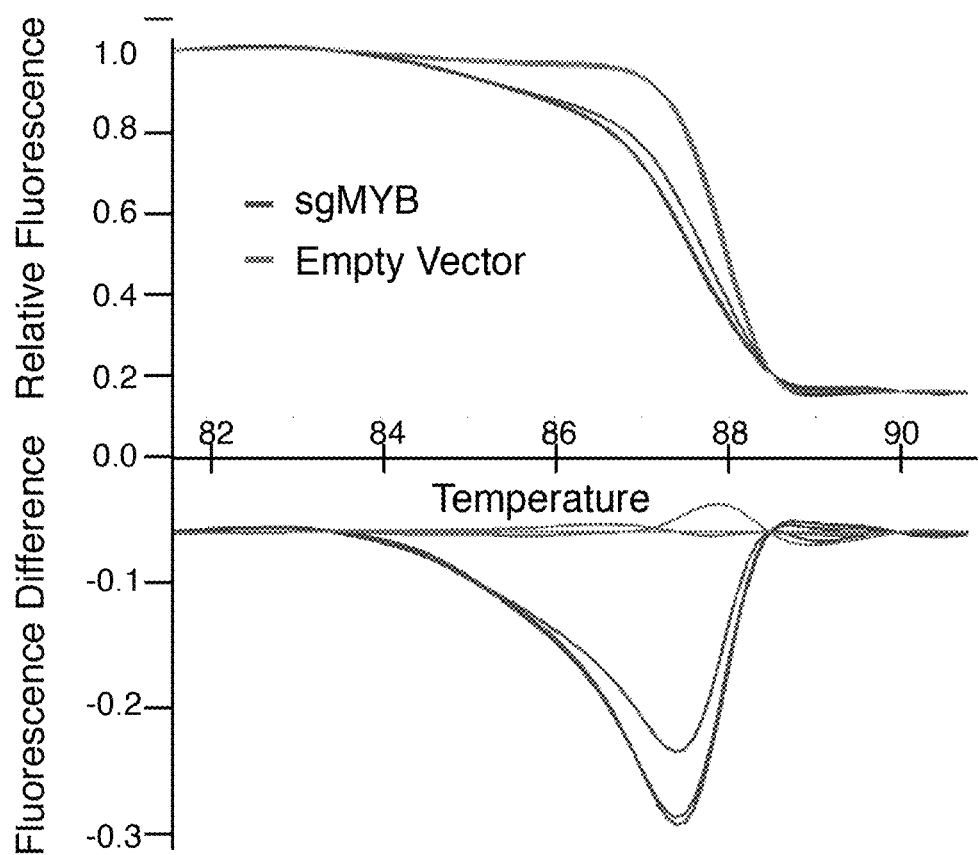
Figure 5C:
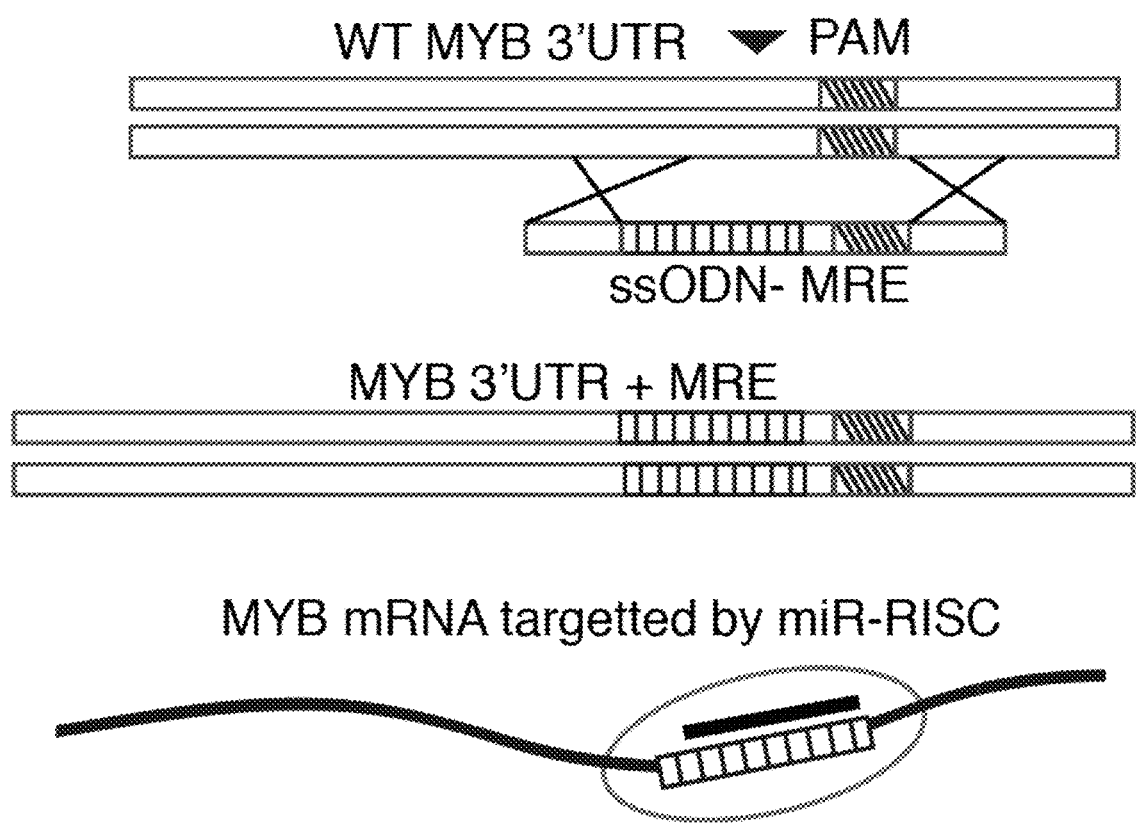
Figure 5D:
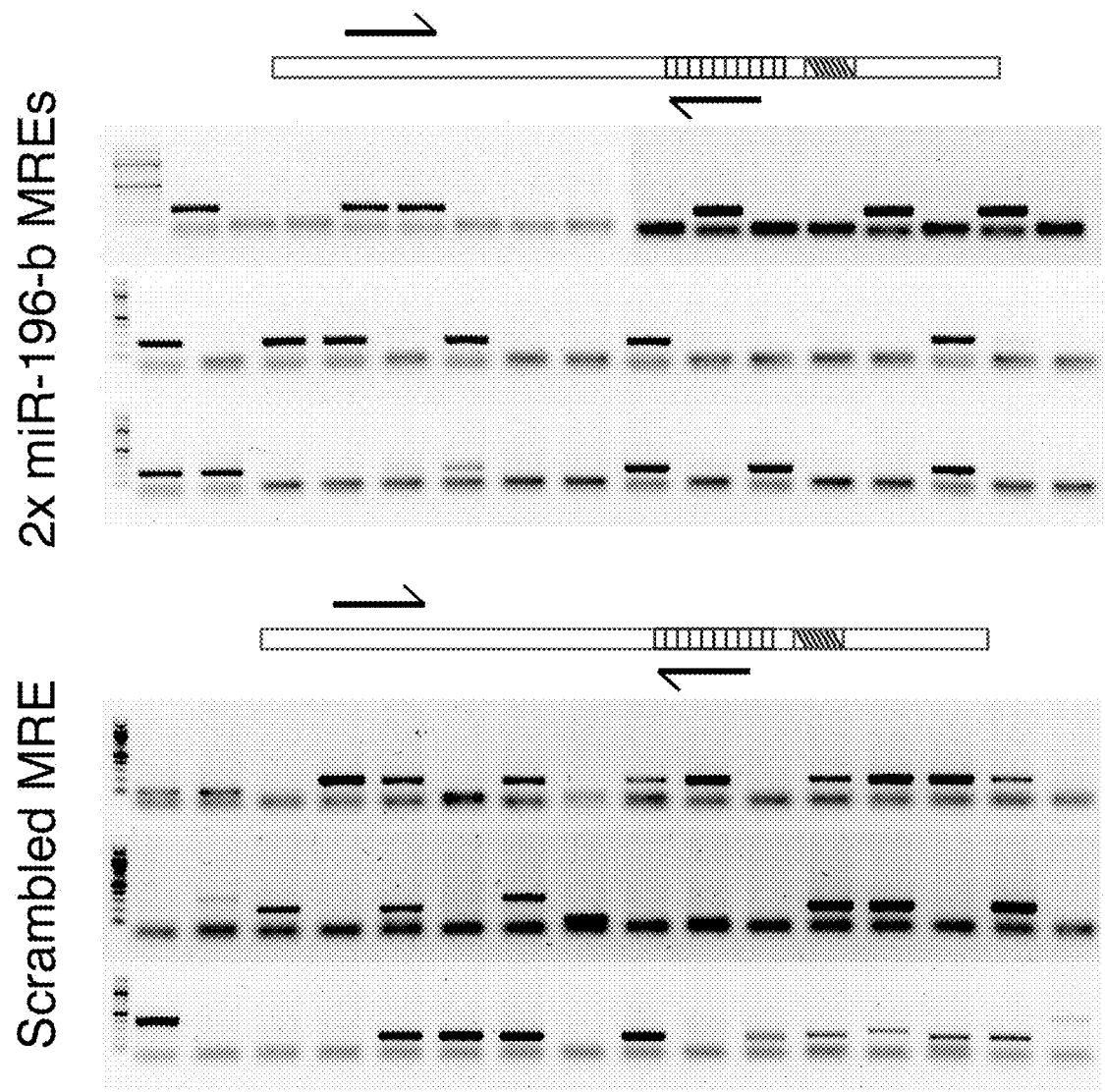
Figure 5E:
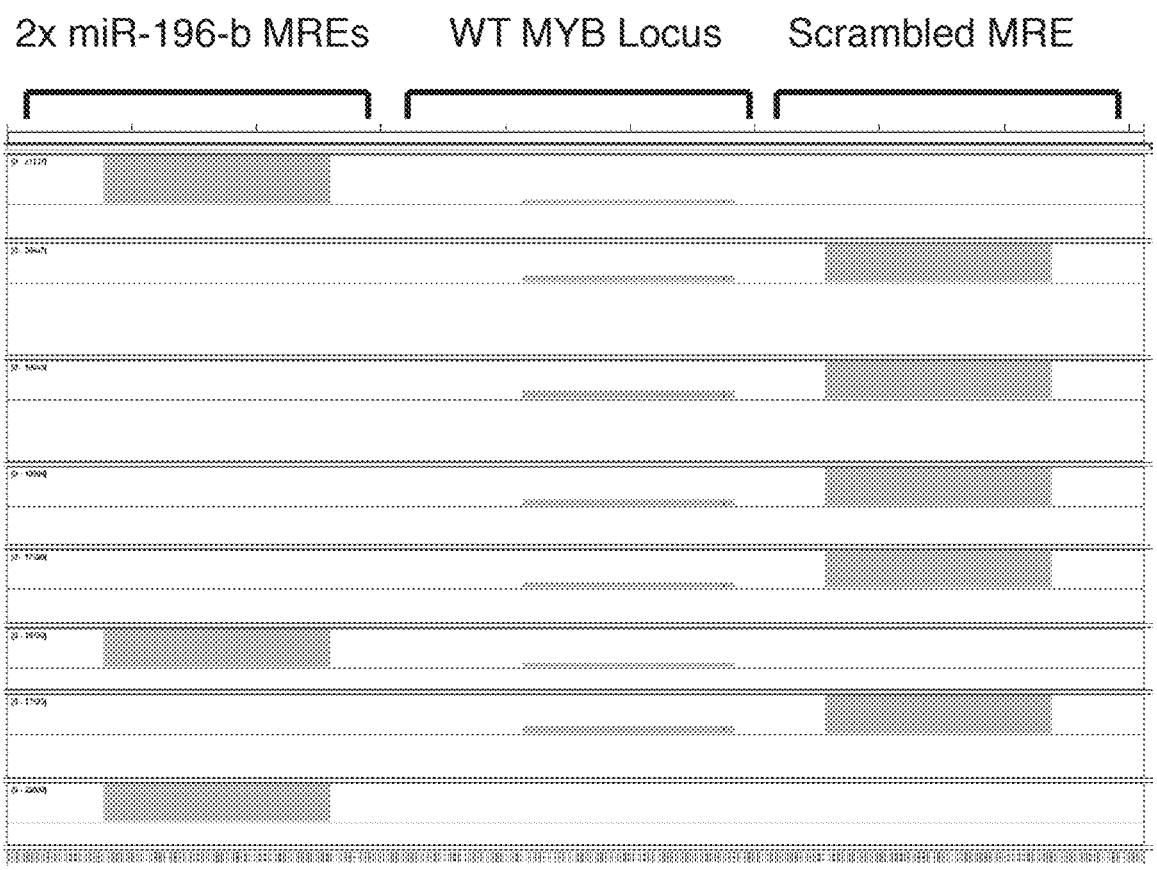

MYB is a transcription factor critical for MLL-AF9 proliferation (28). Because MYB is also necessary for normal embryonic development (40), we designed an MRE to specifically down-regulate MYB in leukemia cells, which over-express miR-196b. We designed three sgRNAs targeting 'MRE-deserts' in the MYB 3'UTR. We tested these sgRNAs in B16-F10 cells and assayed indel formation by HRMA (FIG. 5B). One guide showed very good cutting efficiency, which was subsequently verified by high-throughput sequencing. We used pX459 and ssODNs to insert either two perfect miR-196b target sites, or a "scrambled MRE" into the 3'UTR of MYB in mouse ES cells (mESCs) (FIG. 5C). Following a 7-day puromycin selection, we expanded and genotyped single mES cell clones (FIG. 5D). We detected MRE insertions by PCR in 47/96 clones screened. We analyzed these positive clones by high-throughput sequencing to assess zygosity and fidelity of MRE insertions (FIG. 5E). Five clones contained perfect homozygous insertions of the scrambled MRE and three clones contained perfect homozygous insertions of the miR-196b MRE.

Figure 5F:
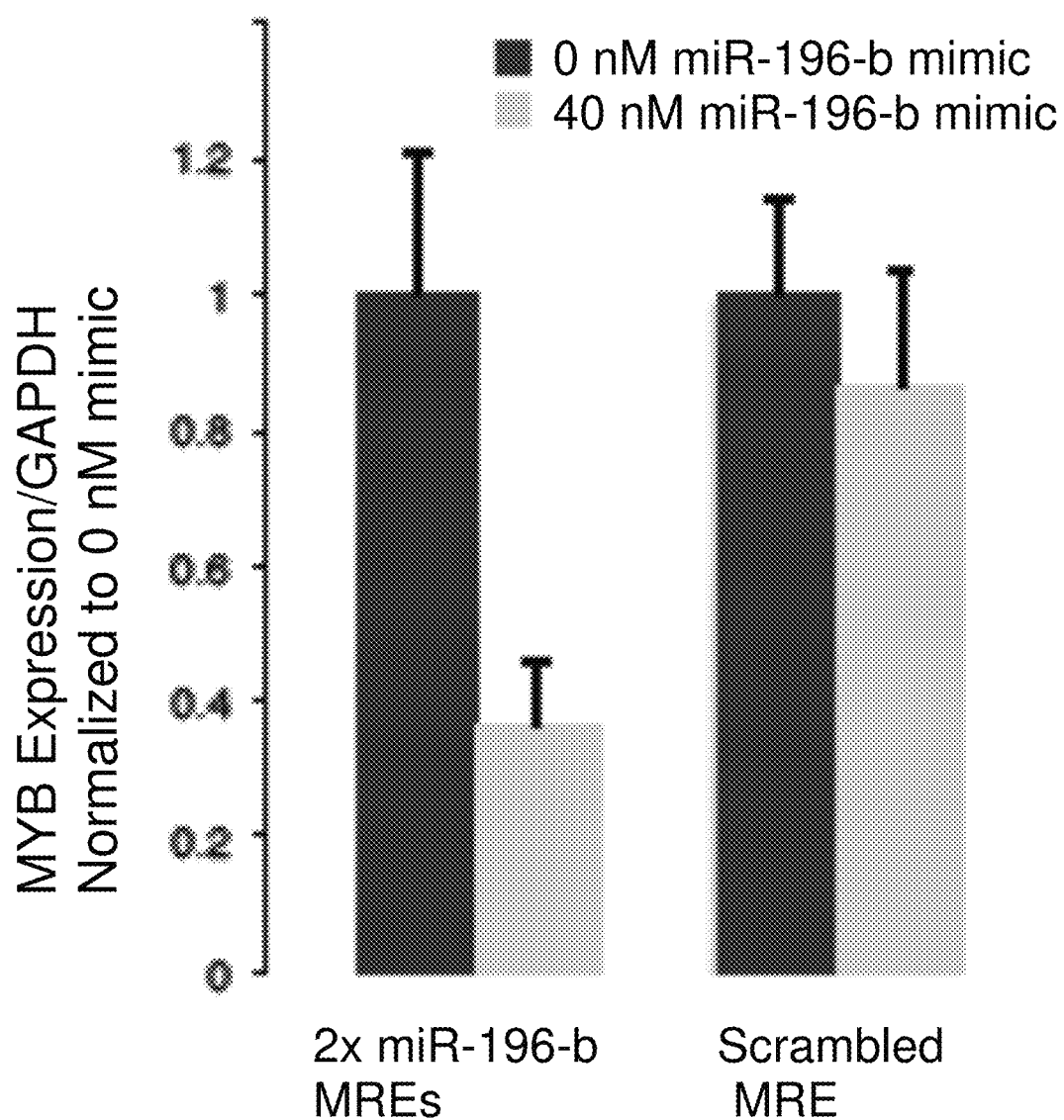

To assess the capacity of this synthetic MRE to silence Myb in a miR-196b-dependent manner, we used the Neon transfection system to introduce a miR-196b mimic (40 nM) in homozygous MRE mESCs (FIG. 5F). We extracted total RNA 12 hours post-transfection and assayed Myb expression by reverse-transcription and quantitative PCR (RT-qPCR). In miR-196b-MRE cells, the microRNA mimic resulted in ~60% repression of Myb (p=0.00014) compared to ~10% repression in the scrambled MRE cells (p=0.71). These results indicate that the artificially-engineered MRE is capable of down-regulating Myb in a miR-196b-dependent fashion.

Next we generated transgenic MRE bearing mice by injecting Cas9 mRNA, sgRNA and ssODN containing 2xmiR196b target sites. F1 progeny generated by crossing a heterozygous founder female with a homozygous founder male were genotyped by PCR to confirm germline transmission and viability of transgenic pups (FIG. 5H). Bone marrow from these mice will be transduced with MLL-AF9 retrovirus to assess leukomegenic initiating potential. We hypothesize that the miR196-MRE will confer resistance to leukemia.

REFERENCES

1. Esteller M (2007) Cancer epigenomics: DNA methylomes and histone-modification maps. Nat Rev Genet 8:286-98.
2. Lee T I, Young R A (2013) Transcriptional regulation and its misregulation in disease. Cell 152:1237-51.
3. Doyle A, McGarry M P, Lee N A, Lee J J (2012) The construction of transgenic and gene knockout/knockin mouse models of human disease. Transgenic Res 21:327-49.

4. Fellmann C et al. (2013) An optimized microRNA backbone for effective single-copy RNAi. Cell Rep 5:1704-13.
5. Chen S-H H, Zhaori G (2011) Potential clinical applications of siRNA technique: benefits and limitations. Eur J Clin Invest 41:221-32.
6. Jackson A L, Linsley P S (2010) Recognizing and avoiding siRNA off-target effects for target identification and therapeutic application. Nat Rev Drug Discov 9:57-67.
7. Bloom R J, Winkler S M, Smolke C D (2014) A quantitative framework for the forward design of synthetic miRNA circuits. Nat Methods.
8. Brown B D et al. (2007) Endogenous microRNA can be broadly exploited to regulate transgene expression according to tissue, lineage and differentiation state. Nat Biotechnol 25:1457-67.
9. Bartel D P (2009) MicroRNAs: target recognition and regulatory functions. Cell 136:215-33
10. Haley B, Zamore P D (2004) Kinetic analysis of the RNAi enzyme complex. Nat Struct Mol Biol 11:599-606.
11. Wee L M, Flores-Jasso C F, Salomon W E, Zamore P D (2012) Argonaute divides its RNA guide into domains with distinct functions and RNA-binding properties. Cell 151:1055-67.
12. Schirle N T, Sheu-Gruttadauria J, MacRae I J (2014) Gene regulation. Structural basis for microRNA targeting. Science 346:608-13.
13. Broderick J A, Salomon W E, Ryder S P, Aronin N, Zamore P D (2011) Argonaute protein identity and pairing geometry determine cooperativity in mammalian RNA silencing. RNA 17:1858-69.
14. Jiang Y, Li Y, Zhu B (2015) T-cell exhaustion in the tumor microenvironment. Cell Death Dis 6:e1792.
15. Pauken K E, Wherry E J (2015) Overcoming T cell exhaustion in infection and cancer. Trends Immunol 36:265-76.
16. Gubin M et al. (2014) Checkpoint blockade cancer immunotherapy targets tumour-specific mutant antigens. Nature.
17. Wolchok J D, Chan T A (2014) Cancer: Antitumour immunity gets a boost. Nature 515:496-8.
18. Tumeh P et al. (2014) PD-1 blockade induces responses by inhibiting adaptive immune resistance. Nature.
19. Powles T et al. (2014) MPDL3280A (anti-PD-L1) treatment leads to clinical activity in metastatic bladder cancer. Nature.
20. Kong Y-C M C, Flynn J C (2014) Opportunistic Autoimmune Disorders Potentiated by Immune-Checkpoint Inhibitors Anti-CTLA-4 and Anti-PD-1. Front Immunol 5:206.
21. Schumann K et al. (2015) Generation of knock-in primary human T cells using Cas9 ribonucleoproteins. Proc Natl Acad Sci USA.
22. Yang H et al. (2013) One-step generation of mice carrying reporter and conditional alleles by CRISPR/Cas-mediated genome engineering. Cell 154:1370-9.
23. Schmitt T M et al. (2004) Induction of T cell development and establishment of T cell competence from embryonic stem cells differentiated in vitro. Nat Immunol 5:410-7.
24. Liang X et al. (2015) Rapid and highly efficient mammalian cell engineering via Cas9 protein transfection. J Biotechnol 208:44-53.
25. De Boer J, Walf-VorderwUlbecke V, Williams O (2013) In focus: MLL-rearranged leukemia. Leukemia 27:1224-8.
26. Popovic R et al. (2009) Regulation of mir-196b by MLL and its overexpression by MLL fusions contributes to immortalization. Blood 113:3314-22.
27. Schotte D et al. (2010) Expression of miR-196b is not exclusively MLL-driven but is especially linked to activation of HOXA genes in pediatric acute lymphoblastic leukemia. Haematologica 95:1675-82.
28. Zuber J et al. (2011) An integrated approach to dissecting oncogene addiction implicates a Myb-coordinated self-renewal program as essential for leukemia maintenance. Genes Dev 25:1628-40.
29. Landgraf P et al. (2007) A mammalian microRNA expression atlas based on small RNA library sequencing. Cell 129:1401-14.
30. Petriv O I et al. (2010) Comprehensive microRNA expression profiling of the hematopoietic hierarchy. Proc Natl Acad Sci USA 107:15443-8.
31. Kuchen S et al. (2010) Regulation of microRNA expression and abundance during lymphopoiesis. Immunity 32:828-39.
32. Rossi R L et al. (2011) Distinct microRNA signatures in human lymphocyte subsets and enforcement of the naive state in CD4+ T cells by the microRNA miR-125b. Nat Immunol 12:796-803.
33. Clarke S R et al. (2000) Characterization of the oval-bumin-specific TCR transgenic line OT-I: MHC elements for positive and negative selection. Immunol Cell Biol 78:110-7.
34. John B et al. (2004) Human MicroRNA targets. PLoS Biol 2:e363.
35. Betel D, Wilson M, Gabow A, Marks D S, Sander C (2008) The microRNA.org resource: targets and expression. Nucleic Acids Res 36:D149-53.
36. Hsu P D et al. (2013) DNA targeting specificity of RNA-guided Cas9 nucleases. Nat Biotechnol 31:827-32.
37. Doench J G et al. (2014) Rational design of highly active sgRNAs for CRISPR-Cas9-mediated gene inactivation. Nat Biotechnol 32:1262-7.
38. Fraley S I et al. (2013) Universal digital high-resolution melt: a novel approach to broad-based profiling of heterogeneous biological samples. Nucleic Acids Res 41:e175.
39. Schotte D et al. (2009) Identification of new microRNA genes and aberrant microRNA profiles in childhood acute lymphoblastic leukemia. Leukemia 23:313-22.
40. Ess K C, Witte D P, Bascomb C P, Aronow B J (1999) Diverse developing mouse lineages exhibit high-level c-Myb expression in immature cells and loss of expression upon differentiation. Oncogene 18:1103-11.
41. Zuris J A et al. (2015) Cationic lipid-mediated delivery of proteins enables efficient protein-based genome editing in vitro and in vivo. Nat Biotechnol 33:73-80.

The invention claimed is:

1. A method of modulating the level of expression of a mammalian gene in a cell, wherein the mammalian gene is expressed or is capable of being expressed in the cell, wherein the cell is one which expresses a microRNA (miRNA) or is capable of expressing the miRNA, the method comprising the steps of:
- (a) producing five or more nucleic acid molecules, each said nucleic acid molecule independently comprising a reporter gene and a different modified heterologous miRNA response element (MRE) in the 3' untranslated region (3'-UTR) of the reporter gene,
- wherein the nucleotide sequence of the reporter gene in each of the nucleic acid molecules is the same,
- wherein the nucleotide sequences of the different modified heterologous MREs have 1, 2, 3, 4 or 5 nucleotide changes with respect to an MRE which is perfectly complementary to the full length of the miRNA, and
- wherein each said modified heterologous MRE binds the miRNA at a different affinity;
- (b) determining the expression level of the reporter gene of each said nucleic acid molecule in the presence of the miRNA, wherein the expression level of the reporter gene of each said nucleic acid molecule is different and wherein the expression level of the reporter gene is distributed across an entire range of from 5% to 90% of an un-silenced control;
- (c) selecting a modified heterologous MRE from the nucleic acid molecules which resulted in or lead to a desired defined reduction of the level of expression of the reporter gene; and
- (d) inserting the selected modified heterologous MRE into the 3'-UTR of the mammalian gene.

2. A method of treating cancer cells in a subject, wherein the cancer cells have the potential of being detected by the immune system, the method comprising the steps of:
- (a) producing five or more nucleic acid molecules, each said nucleic acid molecule independently comprising a reporter gene and a different modified heterologous MRE in the 3'-UTR of the reporter gene,
- wherein the nucleotide sequence of the reporter gene in each of the nucleic acid molecules is the same,
- wherein the nucleotide sequences of the different modified heterologous MREs have 1, 2, 3, 4 or 5 nucleotide changes with respect to an MRE which is perfectly complementary to the full length of an miRNA which is differentially upregulated in activated T-cells,
- wherein each said modified heterologous MRE binds the miRNA at a different affinity;
- (b) determining the expression level of the reporter gene of each said nucleic acid molecule in the presence of the miRNA, wherein the expression level of the reporter gene of each said nucleic acid molecule is different and wherein the expression level of the reporter gene is distributed across an entire range of from 5% to 90% of an un-silenced control;
- (c) selecting a modified heterologous MRE from the nucleic acid molecules which resulted in or lead to a desired defined reduction of the level of expression of the reporter gene;
- (d) in the genome of a T-cell which has been obtained from the subject, inserting the nucleotide sequence of the selected modified heterologous MRE in the 3'-UTR of a gene which encodes an immune checkpoint polypeptide thus producing a modified T-cell; and (e) introducing the modified T-cell into the subject;
wherein the modified T-cell, when activated by contact with the cancer cells, is not negatively regulated by the cancer cells, and wherein the modified T-cell promotes the destruction or rejection of the cancer cells.

3. The method of claim 1, wherein the mammalian gene codes for a transcription factor, chromatin protein, oncogene, receptor, kinase, proto-oncogene or DNA binding protein.

4. The method of claim 1, wherein the miRNA is one which is differentially-expressed in a human disease.

5. The method of claim 1, wherein the selected modified heterologous MRE is positioned in a MRE-desert in the 3′-UTR of the mammalian gene.

6. The method of claim 1, wherein the mammalian gene is selected from the group consisting of MYB, PD-1, LAG-3, TIM-3, BTLA, CTLA-4, HBA1, HBA2 and BCL-2.

7. The method of claim 1, wherein the miRNA is selected from the group consisting of miR-17, miR-19, miR-21, miR-155, miR-196b, miR-92, miR-126 and miR-148a.

8. The method of claim 1, wherein the mammalian gene encodes an immune checkpoint polypeptide.

9. The method of claim 1, wherein step (a) comprises producing ten or more of the nucleic acid molecules.

10. The method of claim 1, wherein step (a) comprises producing fifteen or more of the nucleic acid molecules.

11. The method of claim 1, wherein step (a) comprises producing twenty or more of the nucleic acid molecules.

12. The method of claim 2, wherein step (a) comprises producing ten or more of the nucleic acid molecules.

13. The method of claim 2, wherein step (a) comprises producing fifteen or more of the nucleic acid molecules.

14. The method of claim 2, wherein step (a) comprises producing twenty or more of the nucleic acid molecules.

\* \* \* \* \*